(12) United States Patent
Lambe et al.

(10) Patent No.: US 12,089,845 B2
(45) Date of Patent: Sep. 17, 2024

(54) MEDICAL INTERVENTION DEVICE WITH VERSATILE HANDLE

(71) Applicant: Olympus Corporation, Tokyo (JP)

(72) Inventors: Peter Lambe, Seattle, WA (US); Winslow Harte, Kenmore, WA (US); Bryan Cabatic, Shoreline, WA (US); Razel D. Agustino, Seattle, WA (US); Adam Lee Kosky, Palm Desert, CA (US); David Desmarais, Seattle, WA (US)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 18/048,521

(22) Filed: Oct. 21, 2022

(65) Prior Publication Data

US 2023/0126228 A1    Apr. 27, 2023

Related U.S. Application Data

(60) Provisional application No. 63/270,158, filed on Oct. 21, 2021.

(51) Int. Cl.
*A61B 17/072* (2006.01)
*A61B 17/00* (2006.01)

(52) U.S. Cl.
CPC .......... *A61B 17/07207* (2013.01); *A61B 2017/00398* (2013.01)

(58) Field of Classification Search
CPC ............ A61B 17/07207; A61B 17/068; A61B 17/105; A61B 17/1155
See application file for complete search history.

(56) References Cited

U.S. PATENT DOCUMENTS

| 6,666,854 B1* | 12/2003 | Lange ............... A61B 17/2909 606/1 |
| 8,968,357 B2* | 3/2015 | Mueller ............... A61B 17/29 600/104 |
| 10,172,635 B2 | 1/2019 | Shelton, IV et al. |
| 2007/0078456 A1 | 4/2007 | Dumbauld et al. |
| 2007/0250113 A1* | 10/2007 | Hegeman ............ A61B 1/0055 606/207 |
| 2011/0009864 A1 | 1/2011 | Bucciaglia et al. |
| 2012/0083827 A1 | 4/2012 | Artale et al. |

(Continued)

FOREIGN PATENT DOCUMENTS

| EP | 2822495 | 4/2018 |
| WO | 2023068381 | 4/2023 |

OTHER PUBLICATIONS

"International Application Serial No. PCT JP2022 040278, Invitation to Pay Additional Fees mailed Jan. 20, 23", 12 pgs.

(Continued)

*Primary Examiner* — Nathaniel C Chukwurah
(74) *Attorney, Agent, or Firm* — Schwegman Lundberg & Woessner, P.A.

(57) ABSTRACT

A medical intervention device may include a distal end comprising a pair of jaws and a handle operably coupled to the distal end. The handle may include a pair of pivoting finger arms each having at least one finger loop, the pivoting finger arms being configured for opening and closing the pair of jaws at the distal end. The handle may also include at least one actuation interface arranged on the handle and in a position distal to the pair of finger arms.

18 Claims, 28 Drawing Sheets

(56) References Cited

U.S. PATENT DOCUMENTS

| | | |
|---|---|---|
| 2013/0138102 A1 | 5/2013 | Twomey et al. |
| 2014/0031821 A1 | 1/2014 | Garrison |
| 2015/0272603 A1* | 10/2015 | Shelton, IV ........... A61B 17/29 |
| | | 606/207 |
| 2017/0156747 A1* | 6/2017 | Worrell .............. A61B 17/2816 |
| 2017/0172596 A1 | 6/2017 | Shelton, IV et al. |
| 2019/0125384 A1* | 5/2019 | Scheib ............... A61B 17/2909 |
| 2019/0175187 A1 | 6/2019 | P V R |
| 2019/0307473 A1 | 10/2019 | Fiksen et al. |
| 2021/0282840 A1 | 9/2021 | Rich et al. |

OTHER PUBLICATIONS

"International Application Serial No. PCT JP2022 040278, International Search Report mailed Mar. 14, 23", 7 pgs.
"International Application Serial No. PCT JP2022 040278, Written Opinion mailed Mar. 14, 23", 12 pgs.

\* cited by examiner

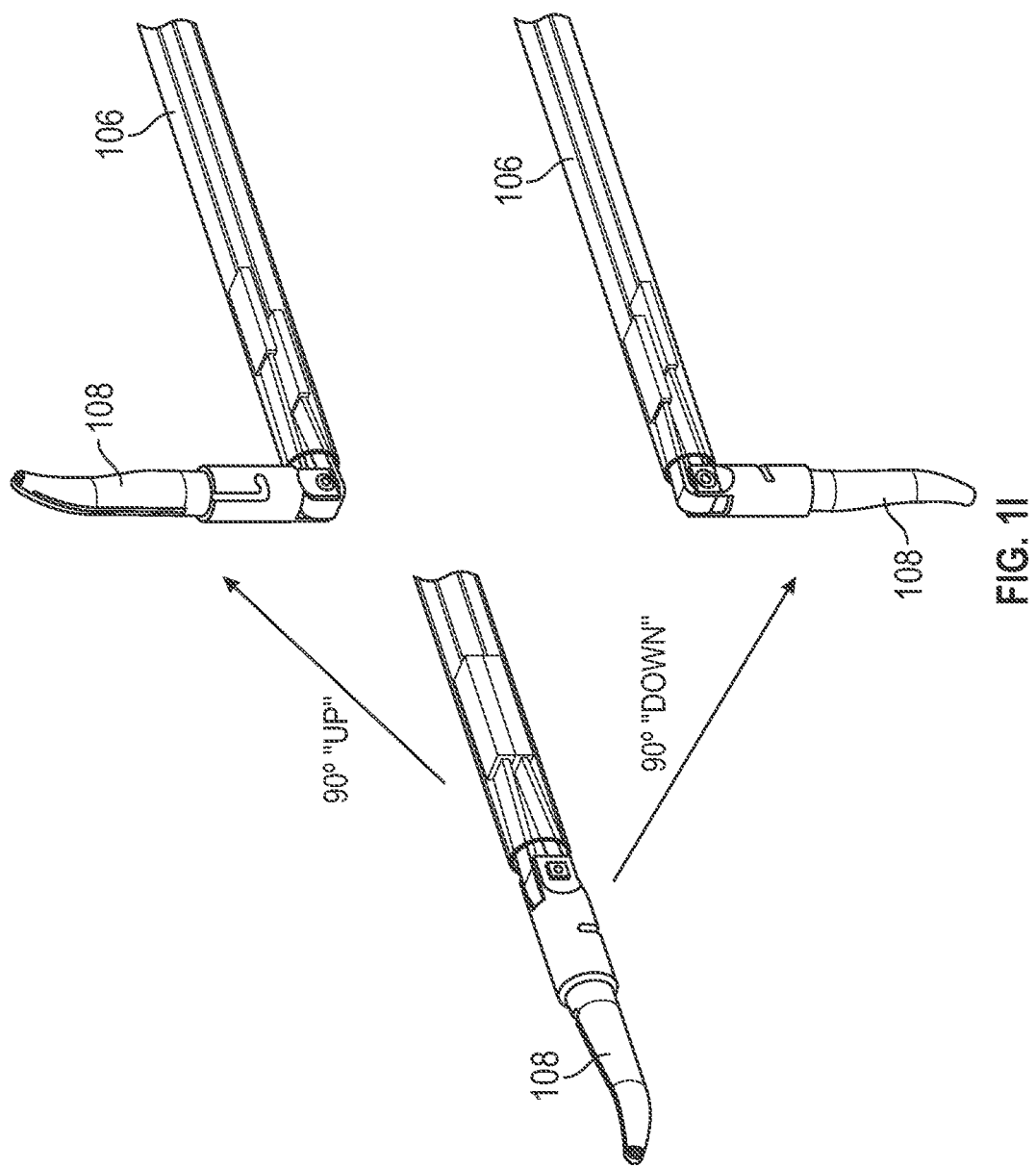

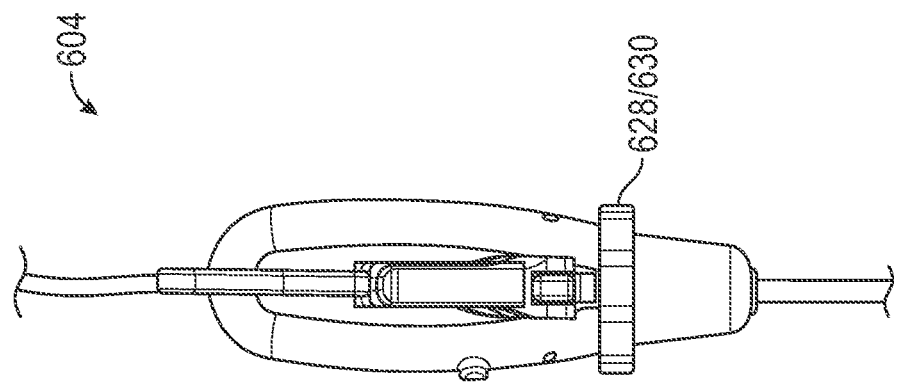
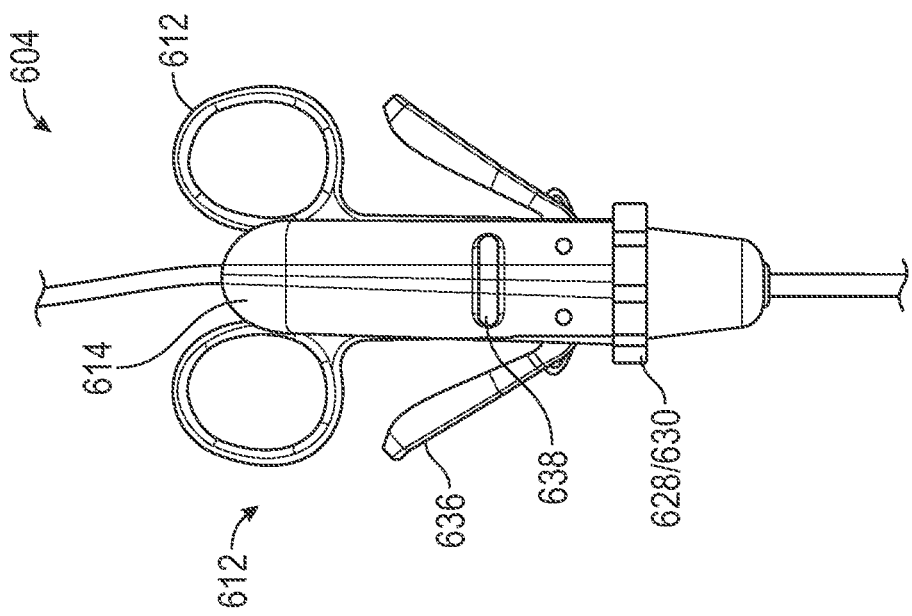
FIG. 9A
FIG. 9B

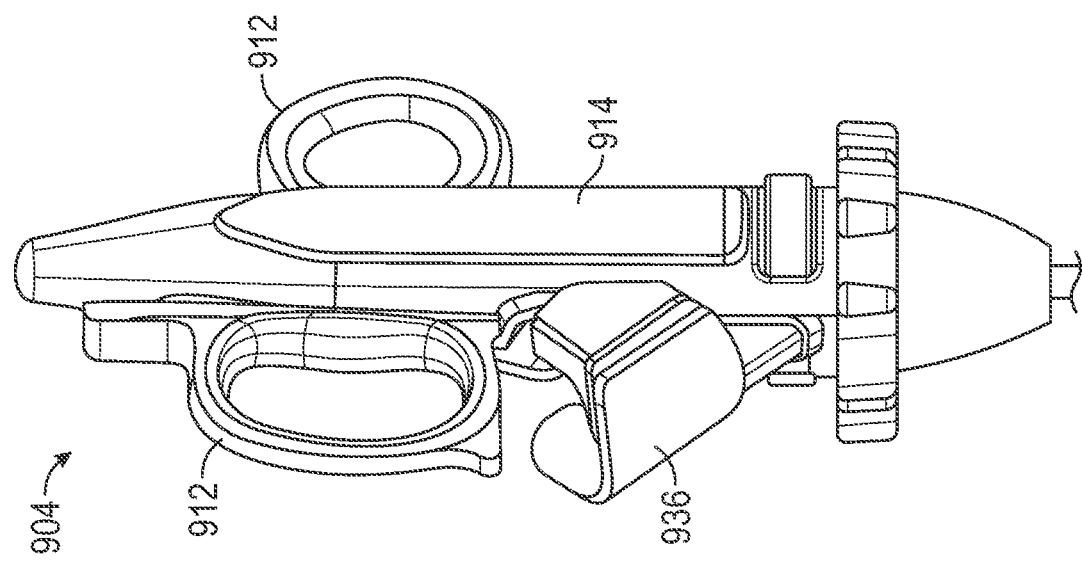
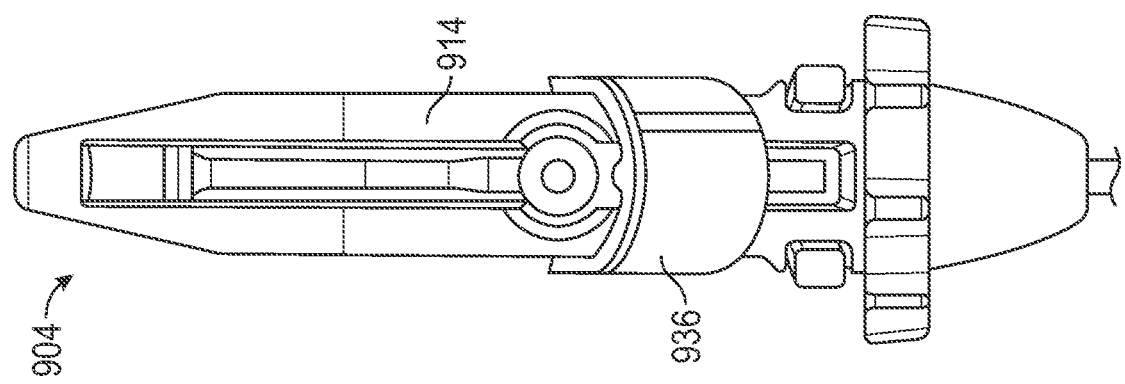

MEDICAL INTERVENTION DEVICE WITH VERSATILE HANDLE

PRIORITY CLAIM

This application claims the benefit of priority to U.S. Provisional Patent Application No. 63/270,158, filed Oct. 21, 2021, the contents of which are incorporated herein by reference in their entirety.

TECHNICAL FIELD

The present application relates to a medical intervention device. More particularly, the present application relates to a medical intervention device having a handle adapted for standard and inverted grip orientations. Still more particularly, the present application relates to a medical device having a rotating and/or articulating distal tip, jaws arranged at the distal tip and adapted for gripping and/or cutting tissue, and/or an energizing feature arranged at a distal tip, where a handle is provided and configured to control the several distal end features and provides standard and inverted grip orientations.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Medical intervention devices may be used for performing medical procedures on patients. In many situations, the intervention device may be adapted for accessing the abdomen, thoracic region, or other portions of the patient's body through a trocar or other port allowing for insertion of the medical intervention device. The intervention device sometimes has a distal end feature that is actuatable by an actuator on a handle. For purposes of accessing the patient through the port, the distal end and a medial portion of the device may be relatively long and slender devices for accessing the patient and the handle may be adapted to remain outside the patient for manipulation by a surgeon to control the distal end feature. For example, pistol grip handles have been provided. In addition, handles akin to those used on a conventional scissor have been provided.

In the case of thoracic surgery, entry into the patient may be through the chest cavity and/or in between one or more ribs of a patient. In these circumstances, the extending portion and distal end of the device may be arranged in a generally vertical orientation to allow access through the port, which may be facing generally upward. A pistol grip or scissor handle may be cumbersome in these circumstances and may cause the surgeon to position his/her forearm vertically with his/her elbow above the port.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

FIG. 1I is a diagram depicting articulation of the distal portion.

FIG. 9A is a side view of a handle portion of a medical intervention device, according to one or more examples.

FIG. 9B is an additional side view of the handle portion of FIG. 9A, according to one or more examples.

FIGS. 11B, 11C, and 11D are perspective views of a distal end of the medical intervention device of FIG. 11A, according to one or more examples.

FIG. 12E is an additional side view of the handle portion of FIG. 12A, according to one or more examples.

FIG. 12F is a perspective view thereof.

Figure 1A:
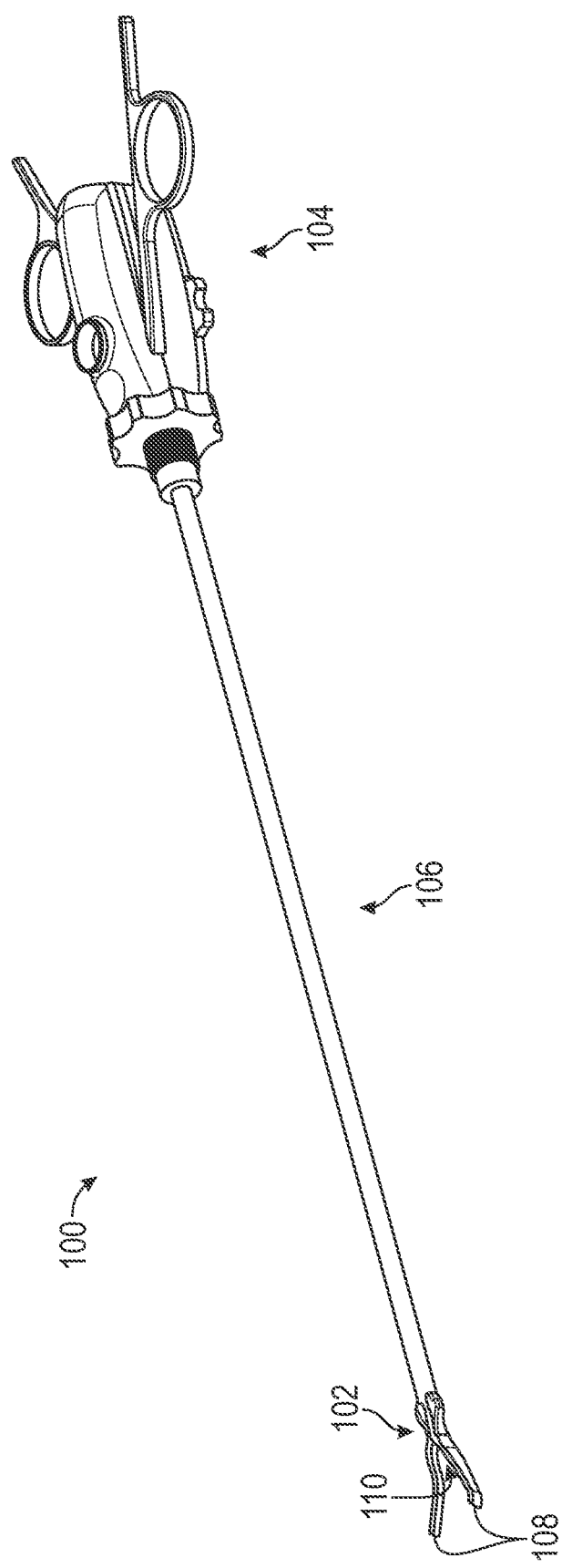
FIG. 1A is a perspective view of a medical intervention device, according to one or more examples.
Figure 1B:
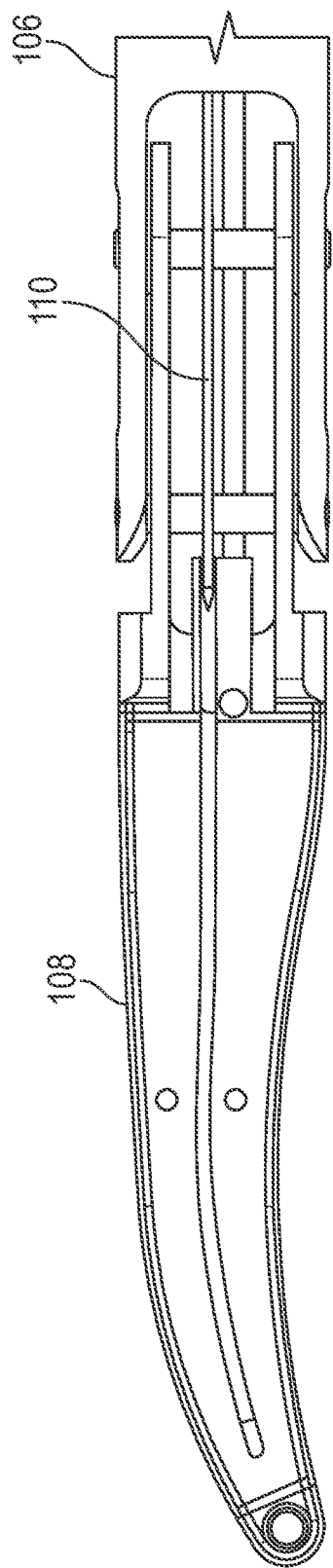
FIG. 1B is a side view of a distal portion of the device of FIG. 1A, with a jaw removed, according to one or more examples.
Figure 1C:
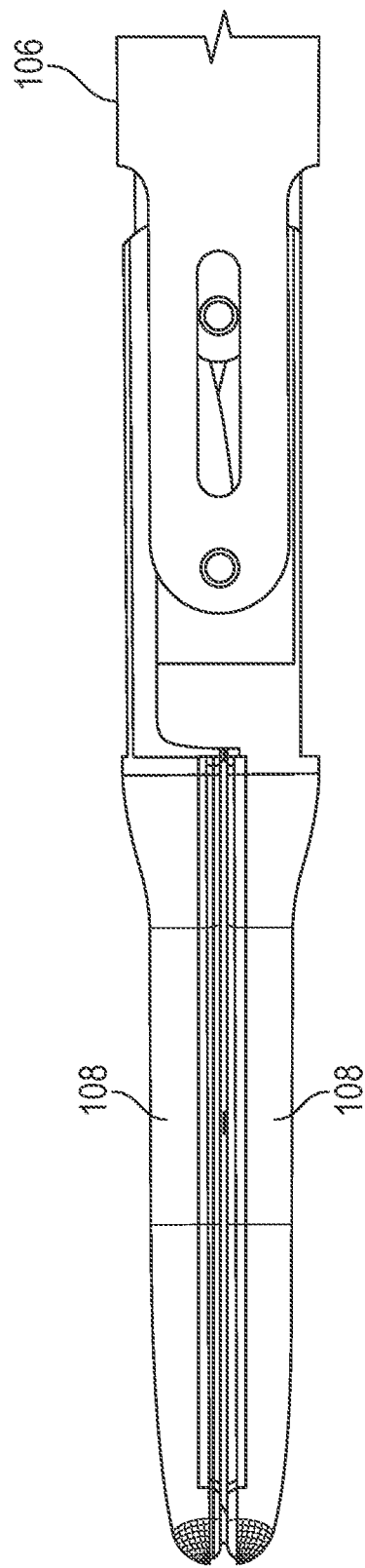
FIG. 1C is a side view thereof.
Figure 1D:
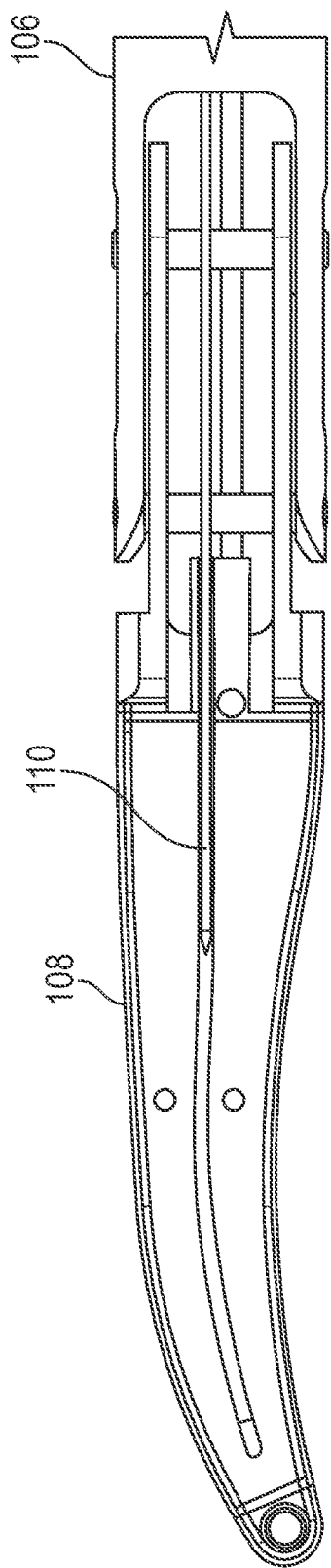
FIG. 1D is a side view of a distal portion of the device of FIG. 1A, with a jaw removed and the blade partially advanced, according to one or more embodiments.
Figure 1E:
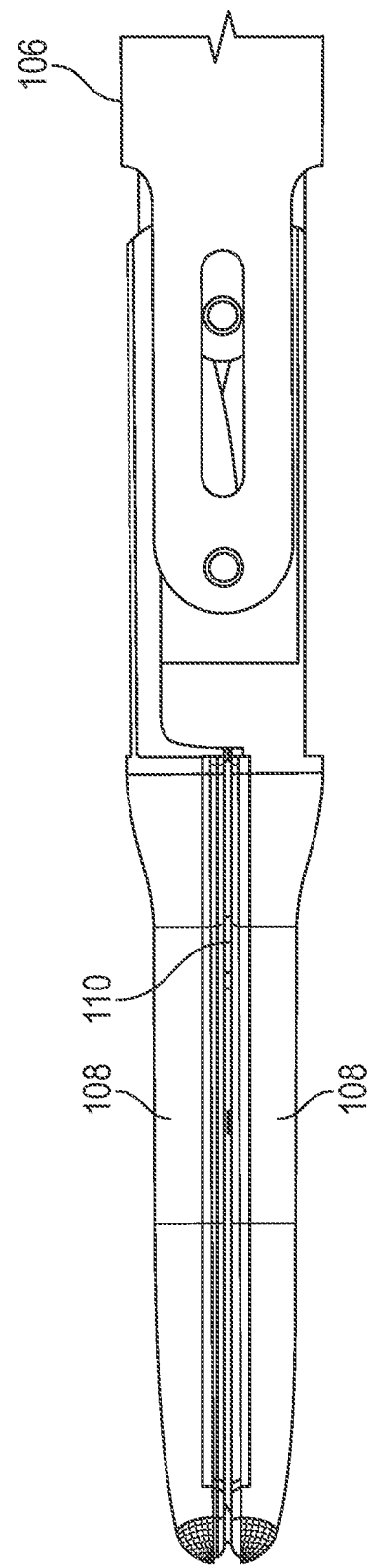
FIG. 1E is a side view thereof.
Figure 1F:
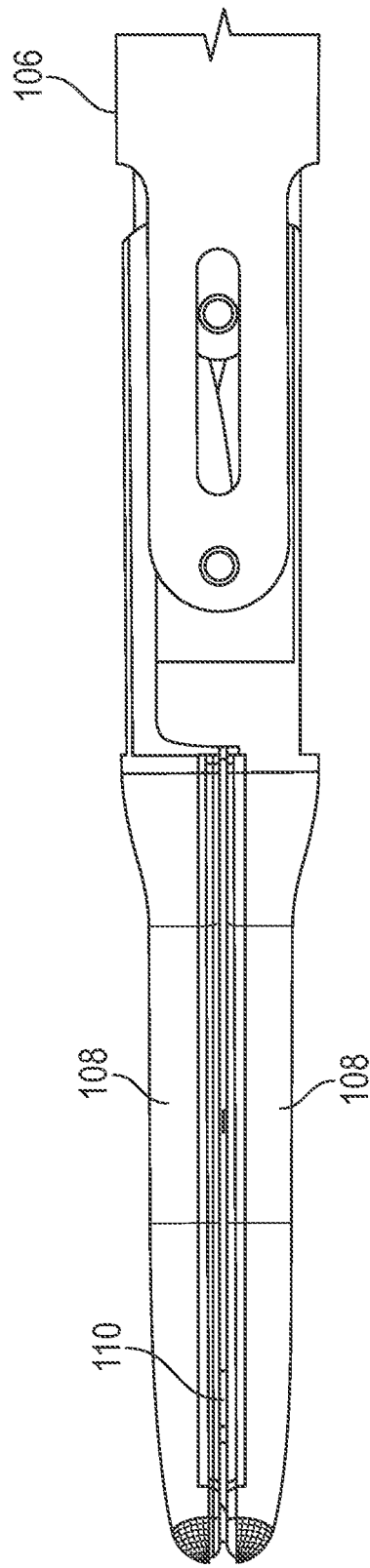
FIG. 1F is a side view thereof with the blade more fully advanced.
Figure 1G:
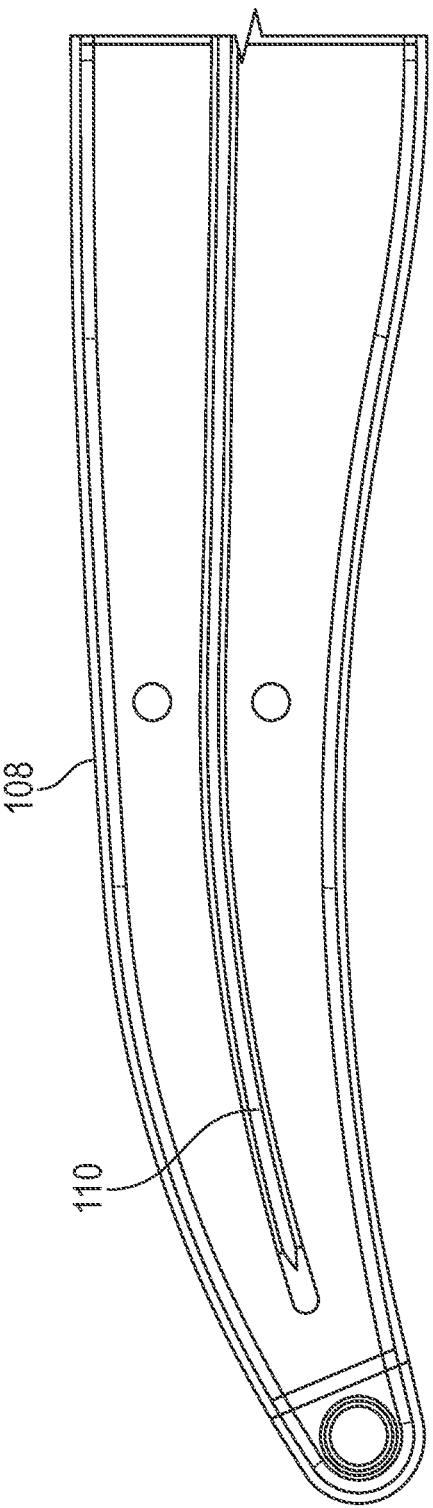
FIG. 1G is a close-up side view thereof with a jaw removed to reveal the blade.

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

The present application, in one or more examples, relates to a medical intervention device with a versatile handle design. In particular, in one or more examples, the handle may include a scissor grip with accompanying actuation interfaces arranged such that the handle may be used in a generally horizontal position or in a generally vertical position while providing access to the actuation interfaces in both positions and while avoiding relatively contorted positions of the user. The medical intervention device may, thus, be used in a wide range of medical interventions. For example, the device may be used by insertion through the side of a patient where the device may be used in a generally horizontal orientation and the user's hand may be in a handshake position. Alternatively, the device may be used by insertion through the chest of a patient where the device may be used in a generally vertical orientation and the user's hand may be in an arm wrestle position. In both orientations, the user's forearm may be arranged generally horizontally or slightly canted up or down. However, an inverted forearm position where the user's elbow is above the user's hand may be avoided.

FIG. 1 is a perspective view of a medical intervention device 100, according to one or more examples. The device 100 may be configured for accessing a surgical site within a patient. In particular, the device may be particularly adapted for entry into the patient through a trocar or other surgical access port. As such, the device may include a distal portion 102 adapted for insertion through the access port, a handle portion 104 configured for remaining outside the patient and for manipulation by the user (e.g., surgeon), and a medial portion 106 extending between the handle 104 and the distal portion 102.

The distal portion 102 may be configured for manipulating, modifying, grasping, cutting, cauterizing, or otherwise interacting with tissues, vessels, organs, or other aspects of a patient's anatomy. In particular, the distal portion 102 may include one or more end effectors for interacting with the patient. As shown, for example in FIGS. 1B-1G, the distal portion 102 may include a pair of jaws 108 and a cutting blade 110. The end effectors may be operable by the handle 104 via mechanical, electrical, or electro-mechanical mechanisms arranged in, on, or extending through the medial portion 106. That is, the mechanisms may extend from the handle 104, through the medial portion 106, and to the distal end 102 where they may function to control the operations of the end effectors. In one or more embodiments, wireless communication between the handle 104 and the end effectors may be provided where physical elements may not extend through the medial portion 106. In other examples, electrical power may extend through the medial portion 106 for powering electro-mechanical devices at the distal end 102 that may be adapted for wireless communication and control by the handle 104. Still other approaches of providing operability of the end effectors by the handle 104 may be provided.

Figure 1H:
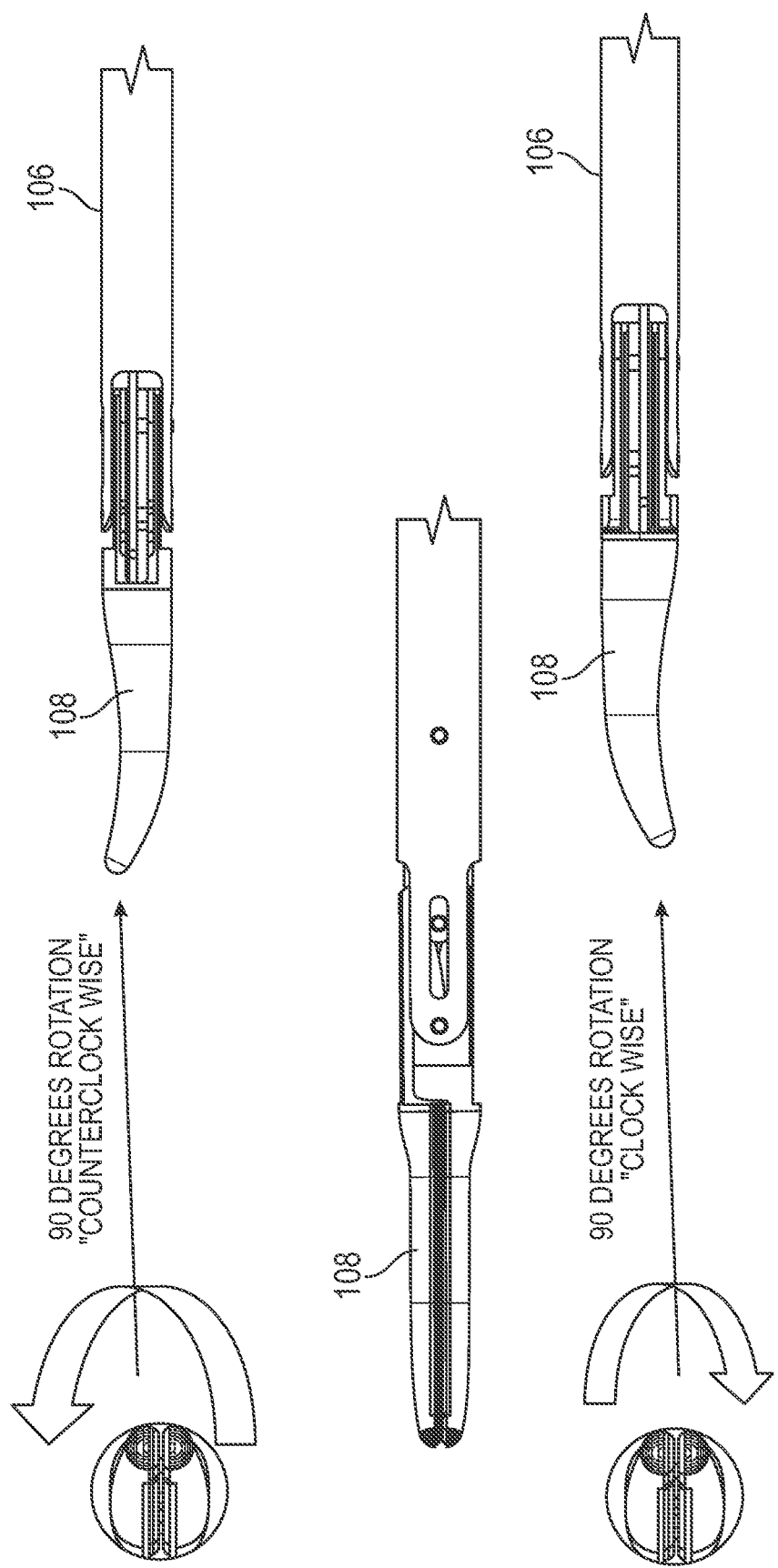
FIG. 1H is a diagram depicting rotation of the distal portion.

With continued reference to FIGS. 1B-1G, the pair of jaws 108 may be adapted for grasping and/or cauterizing tissues, vessels, or other aspects of a patient's anatomy. As shown, the jaws 108 may be hinged jaws that are adapted to pivot relative to one another in an open and closing fashion so as to pinch, grasp, or otherwise gather and/or hold material between them when closed. In one or more embodiments, the jaws 108 may be selectively energized to cause the jaws 108 to cauterize vessels or tissues that are being grasped by the jaws 108. For example, a clamping surface of the jaws may include electrodes allowing current to pass from one jaw, through tissue, and into the other jaw. The jaws 108 may include a slot or other articulation space allowing the cutting blade 110 to pass between the jaws and cut tissues or other aspects of the patient's anatomy. As shown, for example, a slot may be arranged generally centered on each of the jaws and may have a depth equal to or slightly exceeding a blade width. The blade 110 may be arranged on edge so as to articulate longitudinally in a distal/proximal direction between the jaws 108. Moreover, the end effectors may have one or more degrees of freedom beyond open/closing the jaws and longitudinal articulation of the blade. For example, in one or more embodiments as shown in FIG. 1H, the jaws and/or the cutting blade may be configured to rotate about a generally longitudinally extending axis and relative to the other portions of the device. Still further, and as shown in FIG. 1I, the jaws may also be configured to articulate (e.g., pivot together about an axis extending transverse to the device) such that the centerline of open/closing motion is canted relative to the medial 106 portion of the device. Still other types of motion may be provided.

Turning now to FIGS. 2A-9B, several different handles may be described having one or more actuation interfaces corresponding to the several functions of the distal end 102 of the device. It is to be appreciated that while several different examples may be provided, many of the features are not mutually exclusive and could be selected, interchanged, and/or mixed to match the functions of the distal end 102 of the device 100. As such, while particular combinations of actuation interfaces may be described, nothing shall be construed to limit combining an actuation interface or a particular type of actuation interface shown on one example with one or more of the other examples shown.

Figure 2A:
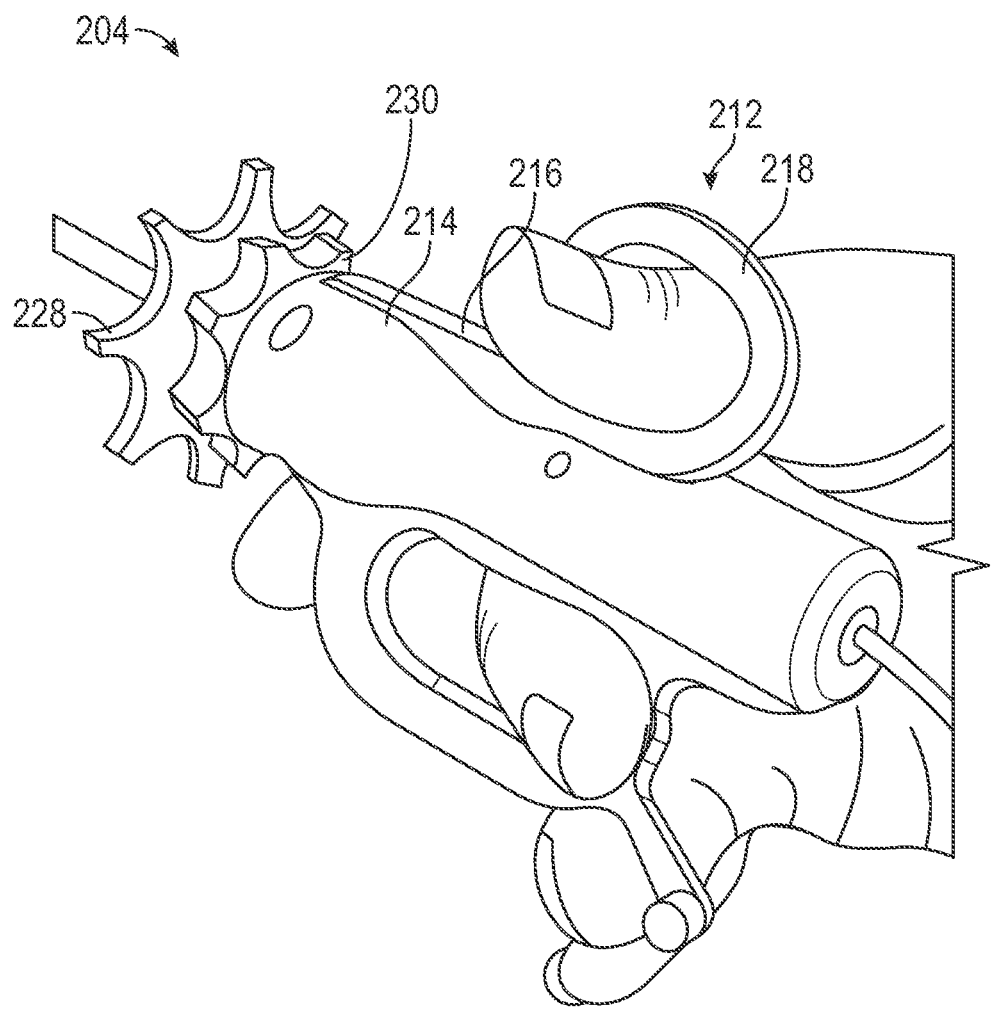
FIG. 2A is a perspective view of a handle portion of a medical intervention device being used generally horizontally, according to one or more examples.
Figure 2B:
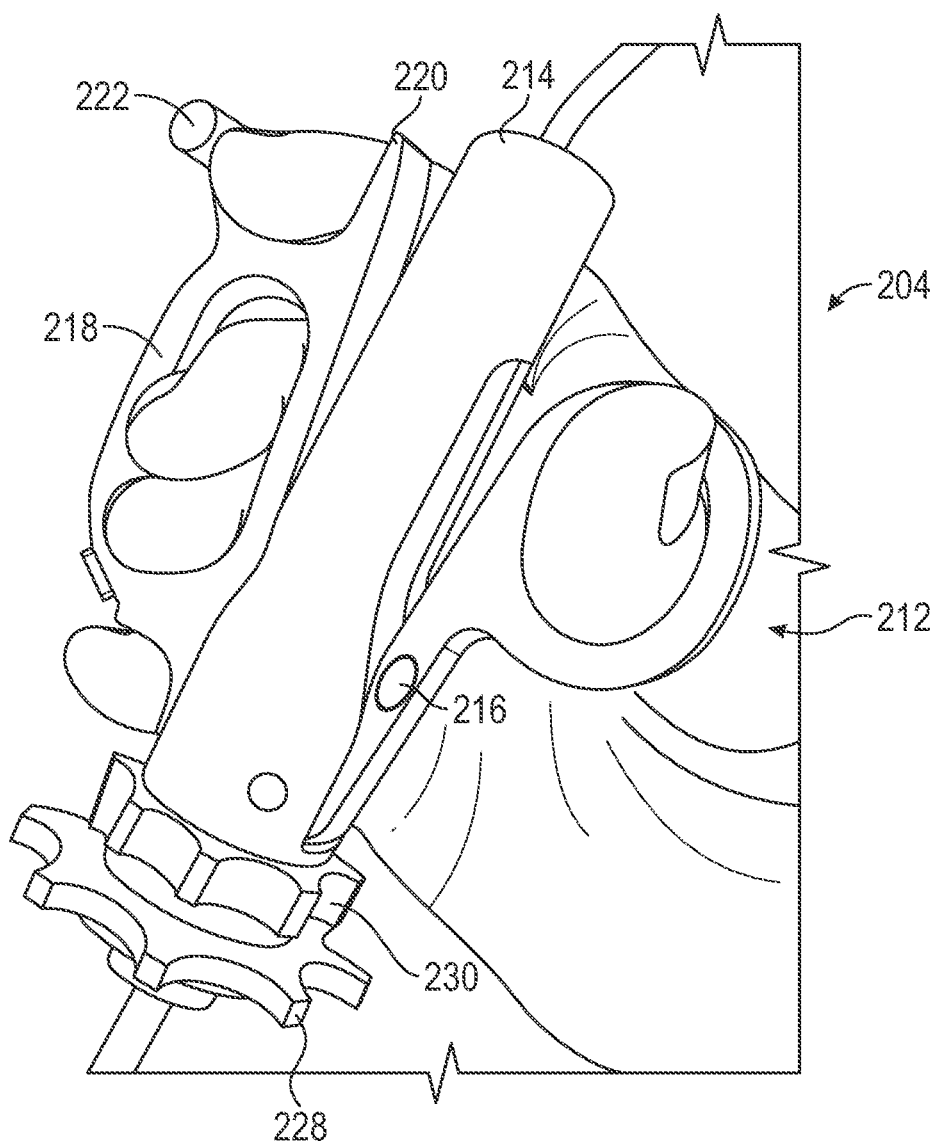
FIG. 2B is a perspective view of the handle portion of FIG. 2A being used generally vertically, according to one or more examples.

As shown in FIGS. 2A and 2B, the handle 204 may include a body portion 214 and a pair of opposing and pivoting arms 212. The arms 212 may include finger loops in the form of single finger loops, double finger loops, or otherwise configured loops. As shown, the present example may include a finger arm 212 having a generally longitudinal bar portion 216, a double finger loop 218 arranged outboard of the bar portion 216, an extension portion 220 where the bar extends passed the double finger loop 218, and a loop tail 222. The present example may also include a thumb arm that includes a generally longitudinal bar portion 216 and a single finger loop 218 arranged outboard of the bar portion 216. As shown by way of comparison of FIGS. 2A and 2B, the handle may be used in a generally horizontal orientation with the user's hand/forearm in a handshake position as shown in FIG. 2A. In this position, the user may place one or more fingers (e.g., index finger, middle finger, ring finger) through the double finger loop and may place an additional finger (e.g., index finger) along the bar portion distal to the double finger loop. Remaining fingers (e.g., ring finger and/or pinky) may be placed on the loop tail 222 or on the extension portion 220. In this position, the user may place their thumb through the single finger loop 218 on the thumb arm. Alternatively, the handle may be used in a generally vertical orientation with the user's hand in an arm wrestle position as shown in FIG. 2B. In this position, the user may place one or more fingers (e.g., middle finger, ring finger, pinky) through the double finger loop 218 and may place an additional finger (e.g., pinky) along the bar portion 216 distal to the double finger loop 218. Remaining figures (e.g., middle finger, index finger) may be placed on loop tail 222 or on the extension portion 220. The user may also place their thumb through the single finger loop 218 on the thumb arm 216.

As may be appreciated, the pivoting arms 212 may function to open and close the jaws 108. That is, when the arms 212 are pivoted away from one another the jaws 108 may open and when the arms 212 are pivoted toward one another the jaws 108 may close. As such, the user experience may be akin to use of a scissor. However, the jaws 108 may be arranged at a distal location from the arms 212 rather than immediately adjacent and/or part of the arms like a scissor. In one or more embodiments, a mechanism for translating the arm motion to the jaw motion may include an arm linkage system 224 as discussed in more detail below with respect to FIG. 3. In other embodiments, a gear system similar to a rack and pinion system may be provided. Still other mechanisms for translating the arm motion to the jaw motion may be provided. In one or more embodiments, the motion of one arm 212 may induce motion of the opposing arm 212. That is, the motion of the arms 212 may be tied together such that neither arm is moveable without motion of the other arm. This may be helpful to maintain control over the distal end of the device where the centerline of the device remains centered between the two arms regardless of what position the arms are in. One example of this type of control is shown in FIG. 3 discussed in more detail below.

Figure 3:
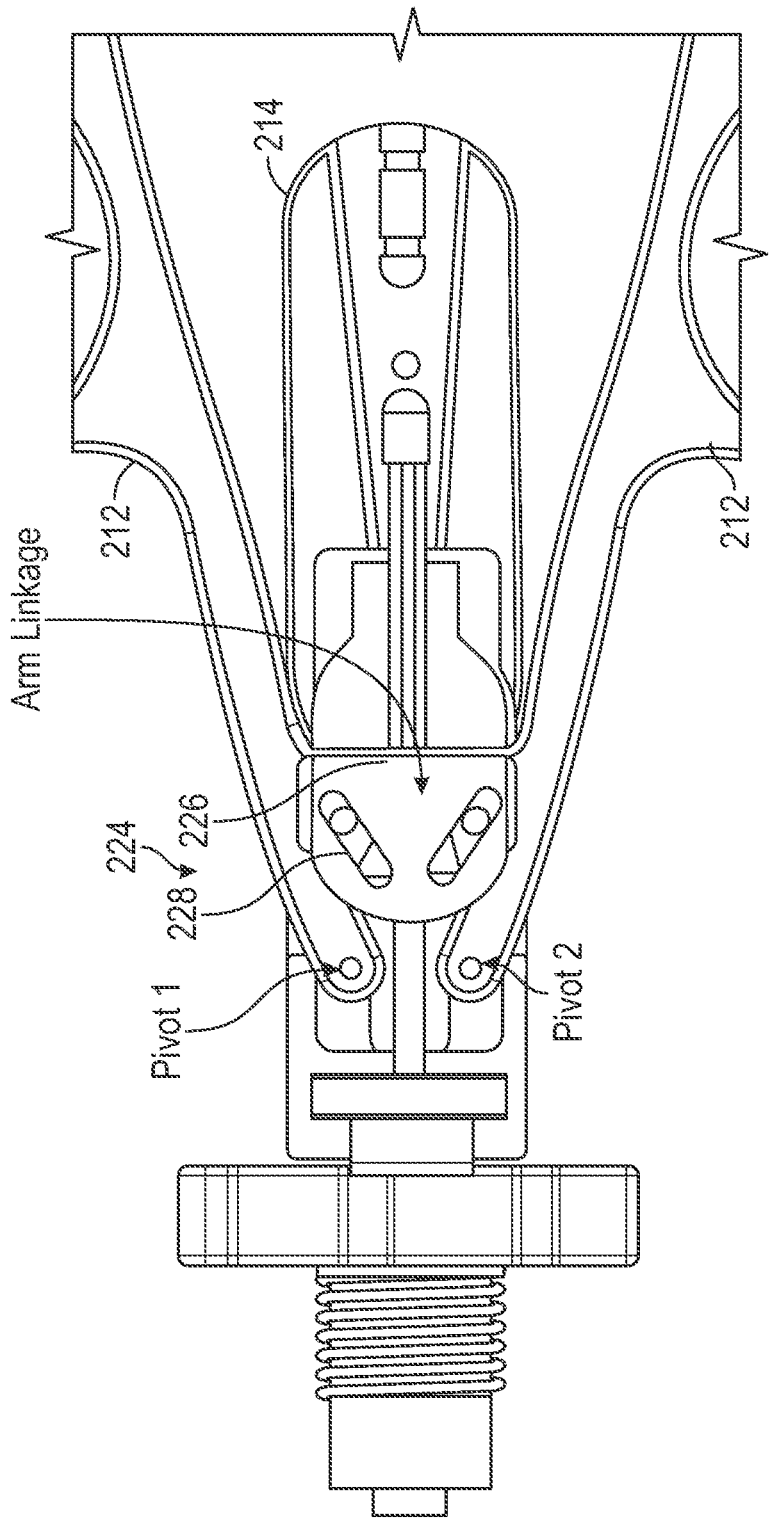
FIG. 3 is a cross-sectional view of a handle portion of a medical intervention device, according to one or more examples.

With reference to FIG. 3, the mechanism for translating the arm motion to the jaw motion is shown. As shown, the mechanism may include an arm linkage system 224. Each arm 212 may be pivotally secured to the body 214 at adjacent but spaced apart pivot points. Each arm 212 may also include a laterally extending pin or a pin extending orthogonally to the plane of pivoting motion of the arms 212. The arm linkage system 224 may include a motion converting slide 226. The motion converting slide 226 may include a pair of spaced apart and diagonally extending slots 228 adapted to receive the pins extending laterally from the arms. The slots 228 may be arranged to converge toward one another as they extend distally and, as such, may form a v-shape pointing in the distal direction. The slots may be spaced apart slightly at the conversion point so as to avoid joining. The motion converting slide 226 may be secured within the body 214 of the handle to restrict its motion to longitudinal motion. That is, the motion converting slide 226 may be arranged in a longitudinally extending shaft, track, or slot, for example. As such, and as shown, when the arms 212 are pivoted outward away from the body 214 of the handle 204, the motion converting slide 226 may be advanced in a distal direction as the pins move outward. When the arms 212 are pivoted toward the body 214 of the handle, the motion converting slide 226 may be pulled in the proximal direction. As such, the motion converting slide may convert reciprocating pivoting motion of the arms 212 to longitudinal reciprocating motion. Moreover, since motion of one arm will translate the motion converting slide 226, this motion will induce motion in the other arm 212 such that both arms will move (e.g., rotate about a pivot point) in unison by a same or similar amount. For example, physically manipulating a single arm 212 by an amount of fifteen degrees of rotation away from the body 214 may cause the other arm 212 to rotate by an amount of fifteen degrees away from the body 214 in an opposite direction. Such embodiments in which the arms 212 are mechanically linked to move in unison have been found to greatly improve stability of the device 100 during surgical procedures. While a motion converting slide 226 has been described, still other systems such as a gear system similar to a rack and pinion system may be provided. Still other mechanisms for translating the arm motion to the jaw motion may be provided such as those described with respect to FIGS. 11A-11R.

Figure 4:
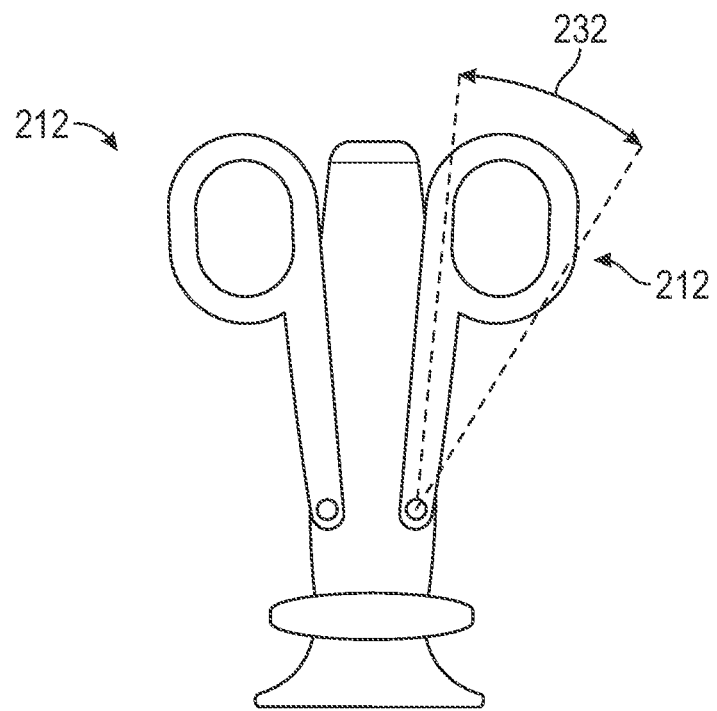
FIG. 4 is a schematic view showing relative motion of actuators on a handle of a medical intervention device, according to one or more examples.
Figure 5:
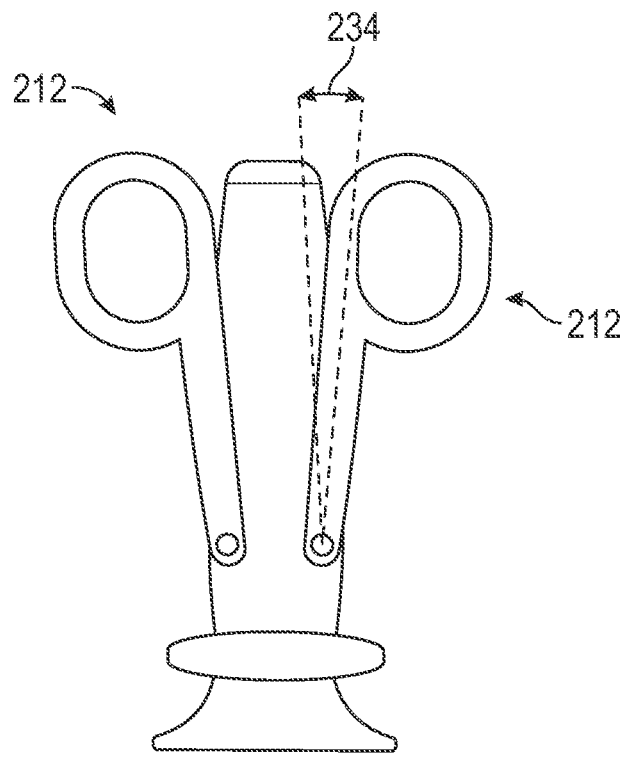
FIG. 5 is a schematic view showing relative motion of actuators on a handle of a medical intervention device, according to one or more examples.

In one or more examples, as depicted in FIGS. 4 and 5, particular ranges of motion of the arms 212 may affect particular actuations of the jaws 108 and/or the cutting blade 110. For example, as shown in FIG. 4, the arms 212 may be opened to a fully open position, which may, in turn, open the jaws 108 at the distal end to a fully open position. The arms 212 may have a first range of motion 232 extending from the fully open position and pivotally inward to a fully closed position where the jaws 108 may be fully closed, but the arms 212 may have a further ability to pivot through a second range of motion 234. For example, the further ability to pivot of the arms 212 or the second range of motion 234 may include 3%-30%, or 5%-15%, or approximately 10% of the full range of motion (e.g., first and second ranges of motion combined 232/234) of the jaws 108. As shown in FIG. 5, the further range of motion 234 of the arms 212 may actuate the cutting blade 110, for example. Mechanically, this may be accomplished by relying on engagement of the motion converting slide 226 to actuate the cutting blade, for example. Alternatively, laterally extending actuation pins that are directly actuated by the inward motion of the arms 212 may be used. In either case, when the arms 212 approach the sides of the body 214 within a particular selected distance, an actuation mechanism operable to advance the cutting blade 110 may be triggered. In one or more embodiments, a safety may be provided on the arm to prevent actuation of the blade without deactivation of the safety. For example, a catch or other mechanism may be arranged on the arms 212 such that further inward motion of the arms is prevented unless/until the safety is deactivated.

This may be a laterally extending tab that may be depressed or recessed into the arm 212 to allow the arm 212 to nest in next to the body or another mechanism for this may be provided.

Referring back to FIGS. 2A and 2B, the handle 204 may also include one or more actuation interfaces. For example, as shown, a rotation control knob 228 and an articulation control knob 230 may be provided. The rotation control knob 228, for example, may be arranged distal to the pair of opposing and pivoting arms 212. In one or more embodiments, the rotation control knob 228 may be rotationally fixed to the medial portion to rotate the medial portion relative to the handle 204 and, as such, rotate the jaws at the distal end of the device. In other embodiments, the rotation control knob 228 may be rotationally fixed to a shaft, coil, or other element extending through the medial portion and coupled to the end effector such that rotation of the rotation control knob 228 rotates the one or more end effectors relative to the medial portion and the handle 204. The rotation control knob 228 may encircle a distal end of the handle 204 and be rotatable relative to the handle via a bearing raceway, low friction joint, or other circumferential joint that allows relative rotation between the handle the rotation control knob 228.

The articulation control knob 230, for example, may be arranged distal to the pair of opposing and pivoting arms 212 and distal or proximal to the rotation control knob 228. In one or more embodiments, the articulation control knob 230 may be operably coupled to the end effector to pivot the end effector about a laterally extending axis (e.g., an axis substantially orthogonal to a longitudinally extending axis of the medial portion). For example, the articulation control knob 230 may be rotationally fixed to a shaft, coil, or other element extending along the medial portion 106. The shaft, coil, or other element may terminate in a gear and an orthogonally arranged gear may be present on the end effector such that rotational motion of the shaft, coil, or other element about the longitudinal axis may be converted to rotational motion about a laterally extending axis. Still other approaches to converting rotational motion of the articulation control knob 230 to articulating motion of the end effector may be provided.

The present embodiment may be advantageous by providing for use of the device in a horizontal or vertical fashion, with differing types of engagement by the hand of the user, while also placing the actuation interfaces in a position that is accessible by the user in either orientation. For example, as shown in FIG. 2A, both the rotation control knob 228 and the articulation control knob 230 are accessible via the index finger of the user. In FIG. 2B, both the rotation control knob and the articulation control knob are accessible via the pinky finger of the user. As such, the user may have the flexibility to use the present device in a wider range of procedures based on the orientation of the entry port for the procedure. That is, the user may be able to use the device for a procedure having a side entry port on a patient, where the user may use the device in a generally horizontal fashion. Alternatively, the user may also be able to use the device for a procedure having a top entry port (e.g., through the rib cage) on a patient, where the user may use the device in a generally vertical orientation.

Figure 6:
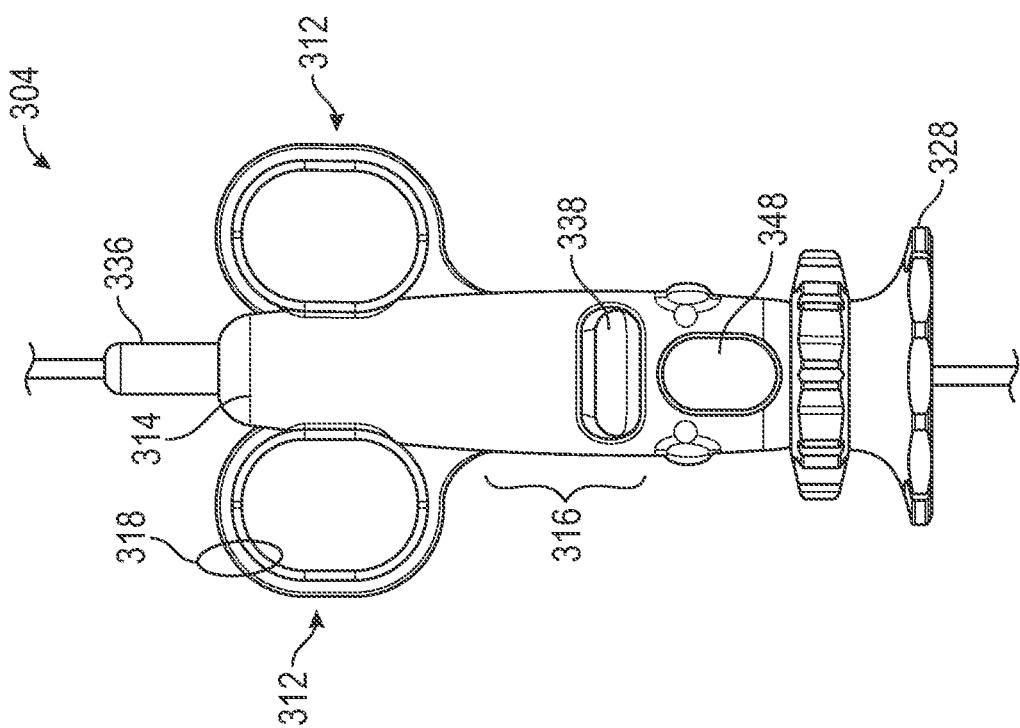
FIG. 6 is a side view of a handle portion of a medical intervention device, according to one or more examples.

Turning now to FIG. 6, another example of a handle 304 for the medical intervention device 100 is shown. As shown, the handle 304 may be much the same as the handle shown in FIGS. 2A & 2B, but the handle may have a slightly different arm configuration and may also include a cutting blade actuation device 336, an energy actuation device 338, and a finger rest 340. It is to be appreciated while a different arm configuration is shown, an arm configuration such as that of FIGS. 2A & 2B may also be provided. Moreover, the inner working elements such as those described with respect to FIGS. 3-5 may also be the same or similar.

As shown, the handle 304 may include a body portion 314 and a pair of opposing and pivoting arms 312. The arms 312 may include finger loops in the form of single finger loops. As shown, the present example may include a finger arm having a generally longitudinal bar portion 316 and a single finger loop 318 arranged at a relatively proximal location on the handle. The present example may also include a thumb arm that includes a generally longitudinal bar portion 316 and a single finger loop 318 arranged at a relatively proximal location on the handle and opposite the finger loop of the other finger arm. The handle may be used in a generally horizontal orientation with the user's hand/forearm in a handshake position. In this position, the user may place a fingers (e.g., a middle finger) through the finger loop and may place an additional finger (e.g., index finger) along the bar portion distal to the finger loop. Remaining fingers (e.g., ring finger and/or pinky) may be placed off the proximal end of the handle or along an actuation interface element such as a cutting device actuator. In this position, the user may place their thumb through the single finger loop on the thumb arm. Alternatively, the handle may be used in a generally vertical orientation with the user's hand in an arm wrestle position. In this position, the user may place a finger (e.g., index finger, middle finger, or ring finger) through the finger loop and may place an additional finger or fingers (e.g., ring finger or pinky) along the bar portion distal to the finger loop. Remaining figures (e.g., middle finger, index finger) may be placed off the proximal end of the handle or along the cutting device actuator.

With continued reference to FIG. 6, the device may include a rotation control knob 328 and an articulation control knob 330 that is the same or similar to like elements on the device of FIGS. 2A and 2B. In addition, the handle 304 may also include a cutting blade actuation device 336. In this embodiment, the actuation device 336 may include a proximal button or plunger. For example, the button or plunger may be arranged on a proximal end of the handle 304 and may be depressible in a distal direction. For example, a user may depress the button with their thumb, for example, when the device is being used in a generally vertical orientation. When the device is being used in a generally horizontal orientation, the button may be depressed with the palm of the hand, for example. The button may be directly or proportionally coupled to the cutting blade 110 such that motion of the button in a distal direction advances the cutting blade 110 in a distal direction by a distance equal to or proportional to the button travel distance. It is to be appreciated that the cutting blade actuation device 336 may be in addition to or an alternative to the cutting blade actuation discussed above with respect to FIGS. 4 and 5. For example, when the device 100 is being used in a generally vertical orientation, the cutting blade actuation device 336 may be relatively accessible by the thumb of a user. However, when the cutting blade actuation device is being used in a generally horizontal orientation, actuation of the cutting blade actuation device may be more easily performed using the arm range of motion rather than the palm of the hand to actuate the button/plunger. This may also be a personal preference of the user as one may not be easier than the other for some users.

In addition, the handle 304 may also include an energy actuation feature 338. The energy actuation feature 338 may include an actuation button or finger sensor arranged on the body 314 of the handle 304. As shown, the button or finger sensor may be arranged distal to the finger loops on the arms 312 and just proximal to the pivot points of the arms 312. Moreover, the button or finger sensor may be arranged on a surface of the body 314 that is circumferentially between the arms. As with the rotation control knob 328 and the articulation control knob 330, the energy actuation feature 338 may be arranged distal to the finger loops and, as such, be accessible by the index finger when the device is being used in a generally horizontal orientation and accessible by the ring or pinky finger when the device is being used in a generally vertical orientation.

Still further, the present example may include a finger rest 340. As shown, the finger rest 340 may include a recessed, cupped, and/or concave area on the surface of the body portion 314 adapted for nested arrangement of a finger tip. As shown, the finger rest 340 may be arranged on the body portion 314 generally between the pivot points of the arms and distally relative to the energy actuation feature 338. When using the device in a horizontal fashion, the user may rest their index finger in the finger rest 340 such that it is poised for actuation of the energy actuation feature 338. When using the device in a generally vertical fashion, the user may rest their ring or pinky finger in the finger rest 340 such that it is poised for actuation of the energy actuation feature 338.

Figure 7:
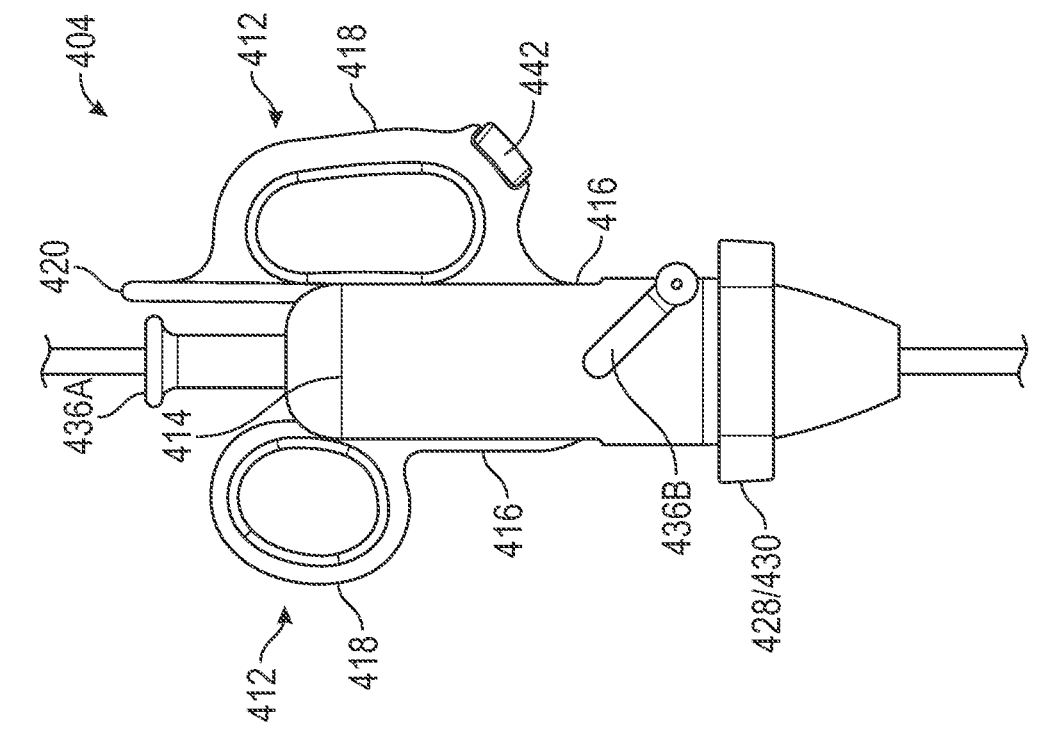
FIG. 7 is a side view of a handle portion of a medical intervention device, according to one or more examples.

FIG. 7 shows yet another example of a handle 404 for a medical intervention device 100 such as that of FIG. 1. This embodiment may share features of the example of FIGS. 2A and 2B as well as the example of FIG. 6 and may also have the same or similar inner working elements such as those described with respect to FIGS. 3-5. Moreover, while particular elements are shown and described, similar elements of the earlier described examples may be substituted for the elements shown.

The arms 412 shown in FIG. 7 may be the same or similar to the arms of FIGS. 2A and 2B. That is, the present example may include a finger arm 412 having a generally longitudinal bar portion 416, a double finger loop 418 arranged outboard of the bar portion 416, an extension portion 420 where the bar extends passed the double finger loop 418. Unlike FIGS. 2A and 2B, the present example may not include a loop tail. Nonetheless, a loop tail may be provided if desired. The present example may also include a thumb arm that includes a generally longitudinal bar portion 416 and a single finger loop 418 arranged outboard of the bar portion. In contrast to the examples of FIGS. 2A, 2B, and 6, the arms 412 and corresponding loops 418 may extend proximal beyond the proximal end of the body 414, for example. A cutting blade actuation device 436A may be arranged on a proximal end of the body 414 of the handle 404 like FIG. 6 and, given the arm configuration, may be arranged generally between the finger loops 418 on the arms 412. As mentioned with respect to FIG. 6, the cutting blade actuation device 436A may be an alternative to or in addition to the actuation of the cutting blade provided by the range of motion of the arms 412. As shown, the finger loop 418 on the double finger loop on the finger arm may include a depressible button 442 on an outboard side thereof. This button may include a cutting blade safety for controlling the range of motion of the arms 412 for actuating the cutting blade apparatus, or this button may include an energy actuation feature. That is, rather than have the energy actuation feature on the body 414 of the handle 404 as shown in FIG. 6, the energy actuation feature may be arranged on the loop of the arm as shown.

The example of FIG. 7 may include yet another cutting blade actuation device 436B in the form of a lever arranged distal to the arms 412. That is, as shown, a rotating lever, knob, or other actuation device may be arranged on a surface of the body 414 of the handle 404 at or near the pivot point of the arms on the body 414 of the handle 404. As shown, the lever may include a central pivot and may include a lever arm with a knob or nub on an end thereof. A user may rotate the lever to actuate the cutting blade 110. It is to be appreciated that, unlike, the coordinated arm motion, actuation of one or more of the cutting blade actuation devices 436A/B, while actuating the cutting blade 110, may not actuated the other actuation device 436A/B. For example, depressing the plunger 436A on the proximal end of the handle 404 may not induce rotation of the lever 436B near the distal end of the handle 404 and vice versa. In one or more embodiments, for example, a longitudinally extending shaft that extends from the handle 404, through the medial portion 106 of the device 100 and to the distal end 102 may be engaged by the one more cutting blade actuation devices 436A/B to actuate the cutting blade 110. However, the cutting blade actuation devices 436A/B may have one-way engagement with the rod such that motion of the rod does not cause actuation of the other actuation device 436A/B. Ledges, ratchets, or other catches may be used to allow the actuation devices 436A/B to engage the rod or other driving device in one direction allowing for the one-way engagement.

As shown, the example in FIG. 7 may include a rotation control knob 430 or an articulation control knob 428. Alternatively, both may be provided.

Figure 8B:
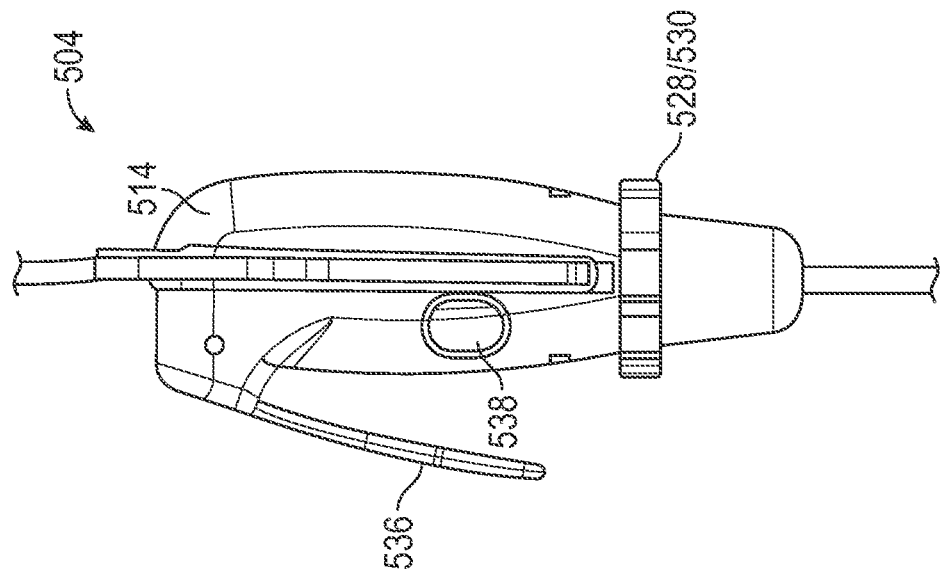
FIG. 8B is an additional side view of the handle portion of FIG. 8A, according to one or more examples.
Figure 8A:
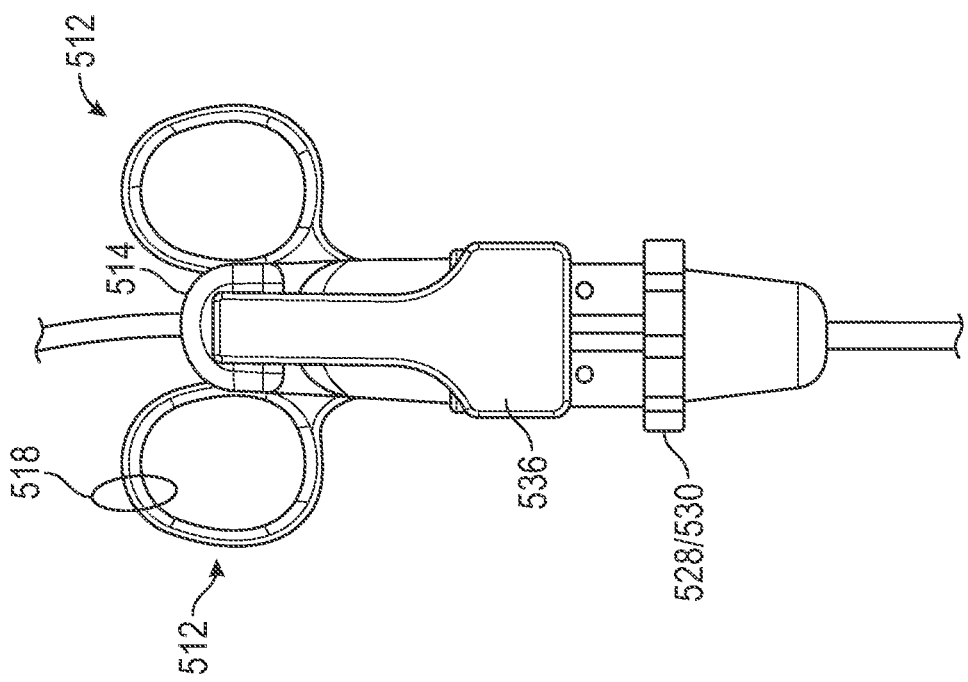
FIG. 8A is a side view of a handle portion of a medical intervention device, according to one or more examples.

FIGS. 8A and 8B show yet another example of a handle 504 for a medical intervention device 100 such as that of FIG. 1. This embodiment may share features of the example of FIGS. 2A and 2B as well as the example of FIGS. 6 and 7 and may also have the same or similar inner working elements such as those described with respect to FIGS. 3-5. Moreover, while particular elements are shown and described, similar elements of the earlier described examples may be substituted for the elements shown.

In the present example, finger arms 512 may be provided that are the same or similar to those described with respect to FIG. 6. However, like FIG. 7, the proximal end of the finger arms and, in particular, the finger loops 518 of the finger arms 512 may extend beyond the proximal end of the housing 514, for example. An energy actuation feature 538 may be provided on the housing 514. The feature may be arranged at or near the pivot point of the finger arms. However, rather than being centered between the finger arms 512 like the example of FIG. 6, the feature may be offset to the side so as to be a bit more accessible relative to the paddle described below. Moreover, while not shown, an additional energy actuation feature on an opposite side of the housing may also be provided. This additional energy actuation feature may correspond to the location of the energy actuation feature shown or a different location may be selected. In addition, a rotation control knob 528, an articulation control knob 530, or both may be provided.

The present example may include a cutting blade actuation device 536 in the form of a paddle. The paddle may be a relatively large paddle mechanism that may be pivotally connected to the handle 504 at a proximal end and may extend distally along and spaced apart from the body 514 of the handle. Pivoting motion of the paddle toward the body 514 of the handle 504 may actuate or drive the cutting blade 110 at the distal end 102 of the device 100. For example, the paddle may include a lever arm that extends into the body 514 of the handle 504 (e.g., generally orthogonally to the paddle). An internal lever may be arranged within the body of the handle and may be supported at its center by a pivot or fulcrum. The lever arm from the paddle may extend into the body, along the internal lever, passed the fulcrum, and may be secured to an end of the internal lever. The drive rod or other driving mechanism of the blade may be secured to an end of the internal lever opposite the connection of the paddle lever. As such, the rearward motion at the location of the connection of the paddle lever to the internal lever, may be converted to forward motion at the opposite end, which may drive the drive rod or other driving mechanism forward. Still other approaches to converting the paddle motion to driving motion of the blade may be provided.

FIGS. 9A and 9B show yet another example of a handle 604 for a medical intervention device such as that of FIG. 1. This embodiment may share features of the example of FIGS. 2A and 2B as well as the example of FIGS. 6, 7, 8A, and 8B and may also have the same or similar inner working elements such as those described with respect to FIGS. 3-5. Moreover, while particular elements are shown and described, similar elements of the earlier described examples may be substituted for the elements shown.

In the present example, finger arms 612 may be provided that are the same or similar to those described with respect to FIG. 7. An energy actuation feature 638 may be provided on the housing 614 that is the same or similar to the energy actuation feature shown on FIG. 6. In addition, a rotation control knob 628, an articulation control knob 630, or both may be provided.

The present example may include a cutting blade actuation device 636 in the form of a pair of lever arms. The lever arms may be arranged generally in plane with the finger arms 612. The lever arms may be somewhat shorter than the finger arms 612 and may have motion that is dependent or independent of the finger arms 612. That is, in one or more embodiments, the lever arms may be pivotally secured to the finger arms 612 such that motion of the finger arms 612 moves the pivot point of the lever arms and, as such, moves the lever arms. Alternatively, the lever arms may be pivotally secured to the body 614 at the same position of the finger arms 612 or a different position than the finger arms 612. In either of these situations, motion of the finger arms 612 may not cause motion of the lever arms. However, in one or more embodiments, a biasing mechanism may be provided between the lever arms and the finger arms 612 such that motion of the finger arms 612 causes motion of the lever arms and relative motion between the finger arms 612 and lever arms may occur when the biasing force is overcome. Actuation of the lever arms may occur by squeezing the lever arms toward the body of the handle. In one or more embodiments, motion of the lever arms relative to the body may actuate the cutting blade 110. In other embodiments, motion of the lever arm relative to the finger arms 612 may actuate the cutting blade. In one or more embodiments a safety mechanism may be provided that prevents actuation of the cutting blade 110 unless/until the jaws 108 of the device 100 are closed or close to being closed. In this embodiment, for example, actuation of the lever arms relative to the body 614 or relative to the finger arms 612 (as the case may be) may be prevented or resisted unless/until the finger arms 612 close to within a selected range of motion that is deemed closed. In one or more embodiments, this safety may be in the form of the biasing mechanism between the lever arms and the finger arms 612. That is, the biasing mechanism may be stiff enough that the lever arms are held in an unactuated position unless until the finger arms 612 fully close and a force is able to develop to overcome the biasing force. That is, if the lever arms are depressed when the finger arms 612 are open, this may cause the finger arms 612 to close rather than cause relative motion between the lever arms and the finger arms 612. Relative motion between the lever arms and the finger arms 612 may not occur unless/until the finger arms 612 fully close and reach a stopping point. This safety mechanism may help to ensure, for example, that tissue to be cut is firmly grasped by the jaws 108 before the cutting blade 110 is advanced and may prevent advancement of the cutting blade 110 in an unprotected or unguided condition. That is, as discussed above, the jaws 108 may include grooves or slots that guide the cutting blade 110 and when the jaws 108 are open, advancement of the blade 110 may cause the blade 110 to be subject to lateral bending forces due to lack of support from the grooves or slots and may otherwise expose the blade 110 to cutting unintended tissues, vessels, or other aspects of a patient's anatomy, for example. Still other approaches to providing a safety mechanism for actuation of the cutting blade 110 may be provided.

Figure 10:
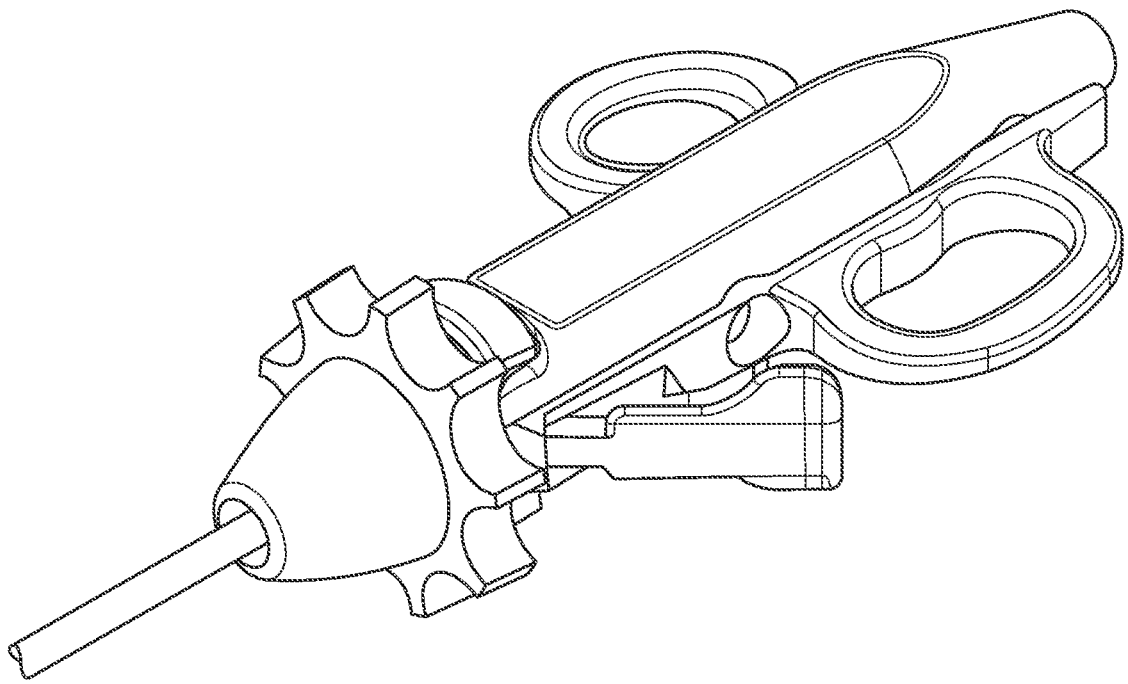
FIG. 10 is a perspective view of a handle of a medical intervention device, according to one or more examples.
Figure 11A:
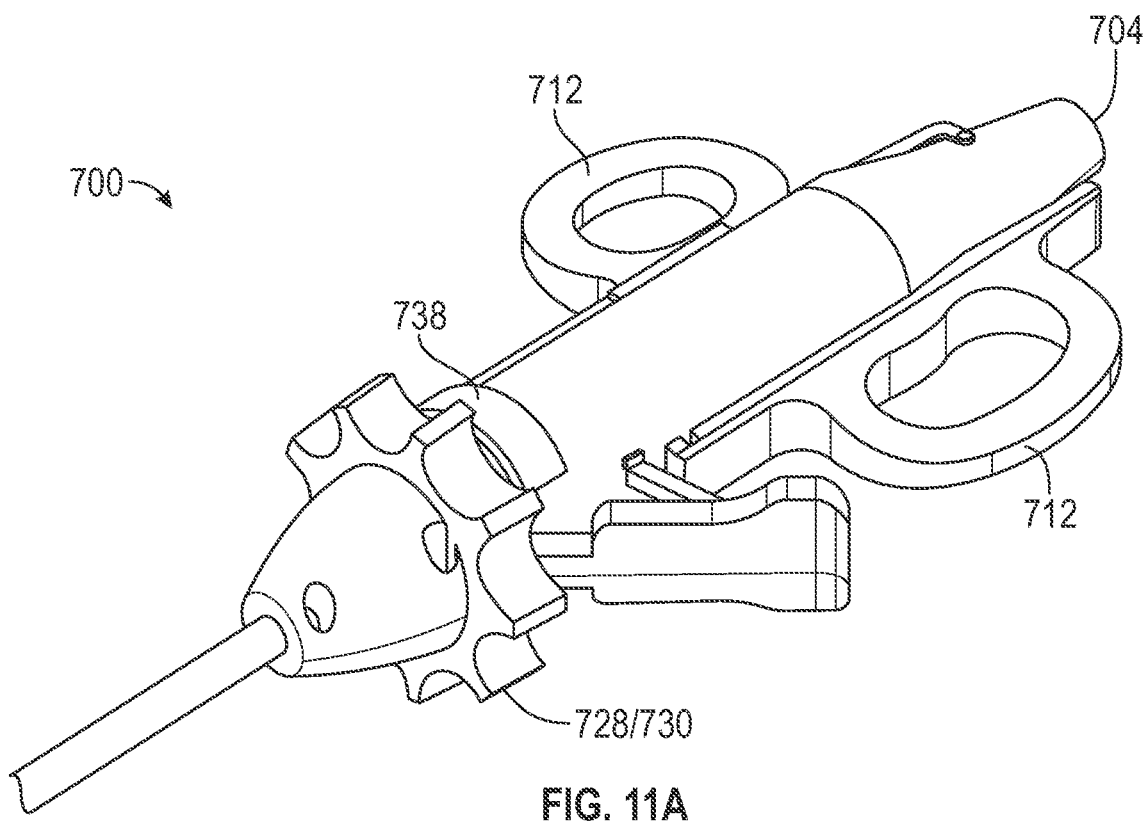
FIG. 11A is a perspective view of a handle of a medical intervention device, according to one or more examples.
Figure 11D:
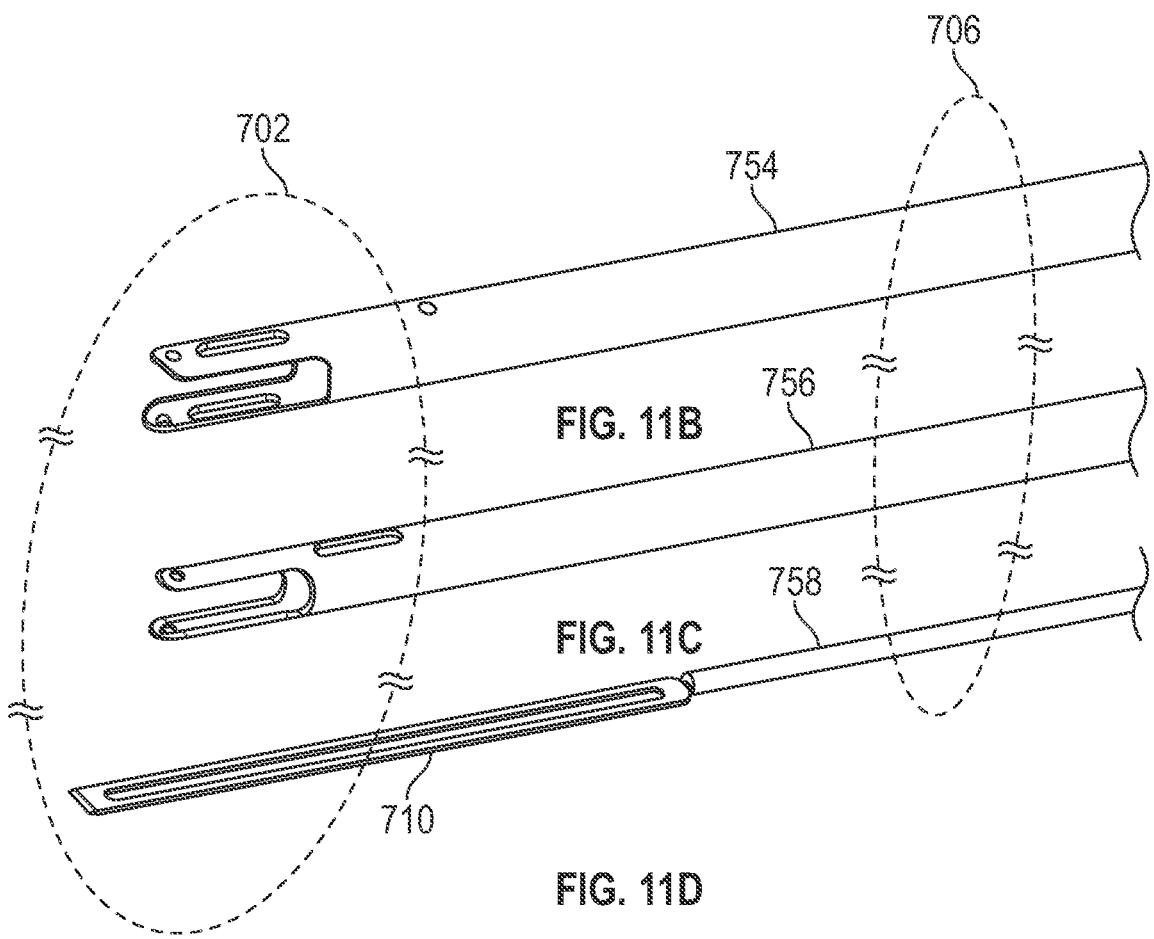
Figure 11E:
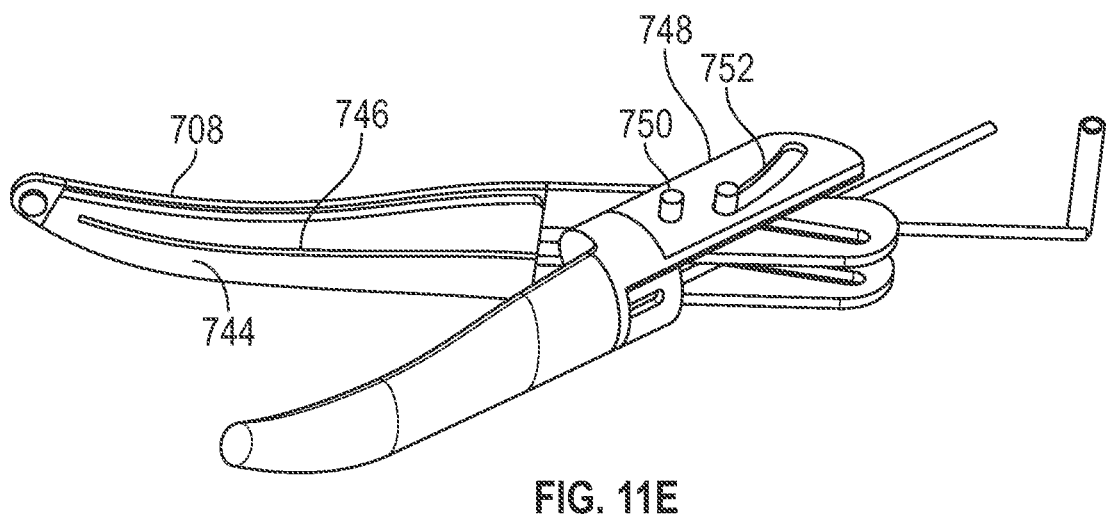
FIG. 11E is a perspective view of a distal end jaws of the medical intervention device of FIG. 11A, according to one or more examples.
Figure 11F:
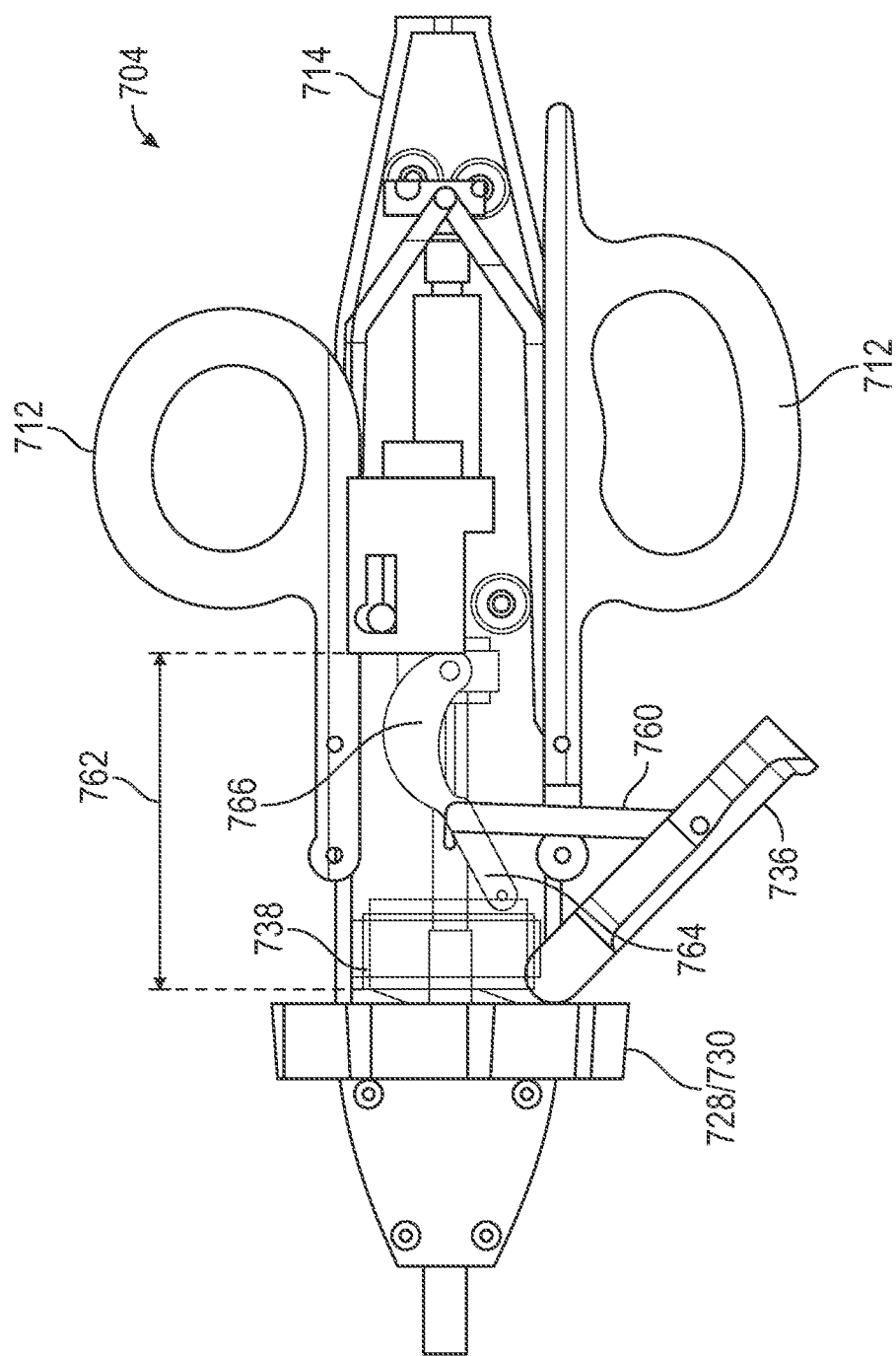
FIG. 11F is a transparent view of a handle of the medical intervention device, according to one or more examples.
Figure 11G:
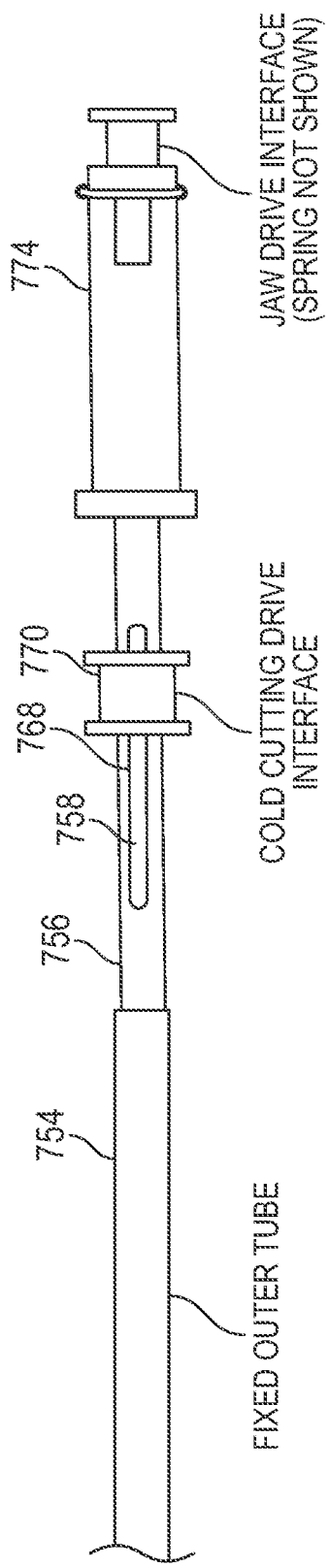
FIG. 11G is a side view of a drive interface and a jaw drive interface each arranged on an inner housing, according to one or more examples.
Figure 11H:
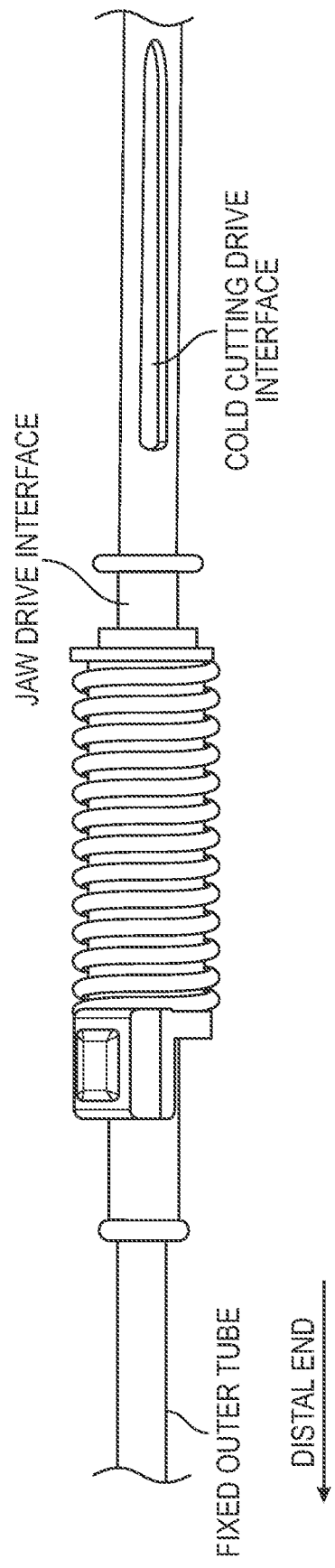
FIG. 11H is an additional view of the jaw drive interface thereof.
Figure 11I:
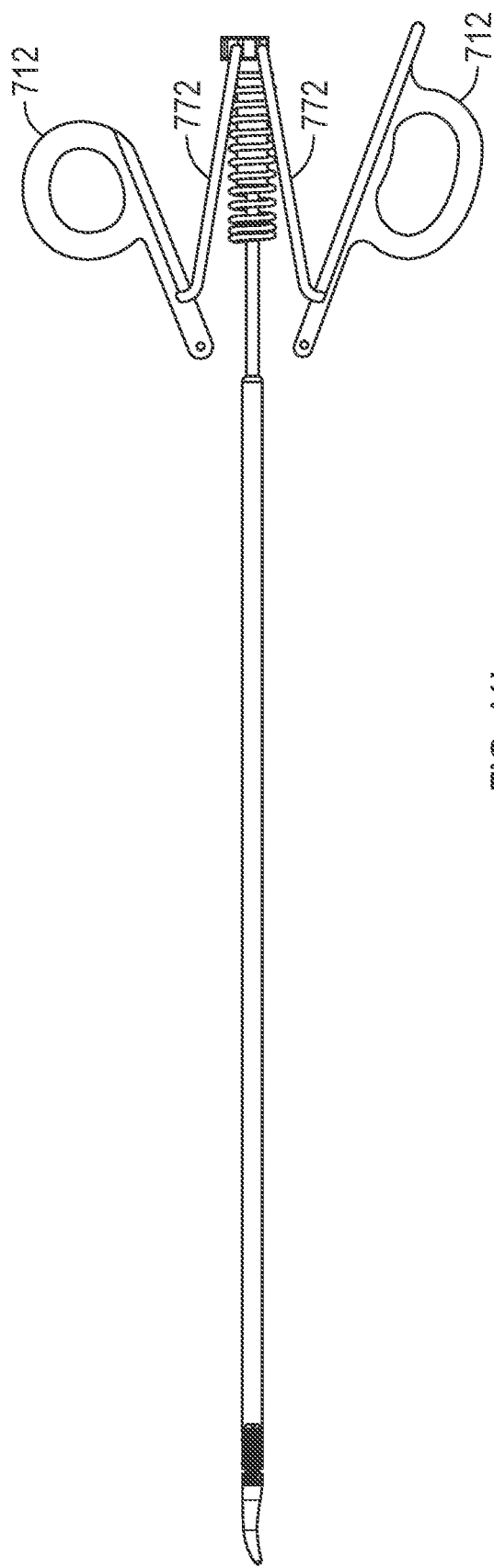
FIG. 11I is a side view of several jaw actuation mechanisms, according to one or more examples.
Figure 11J:
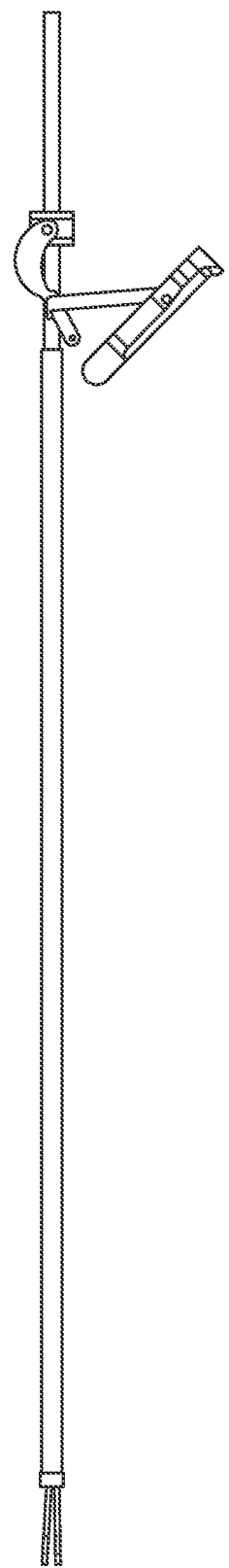
FIG. 11J is a side view of several blade actuation mechanisms, according to one or more examples.
Figure 11K:
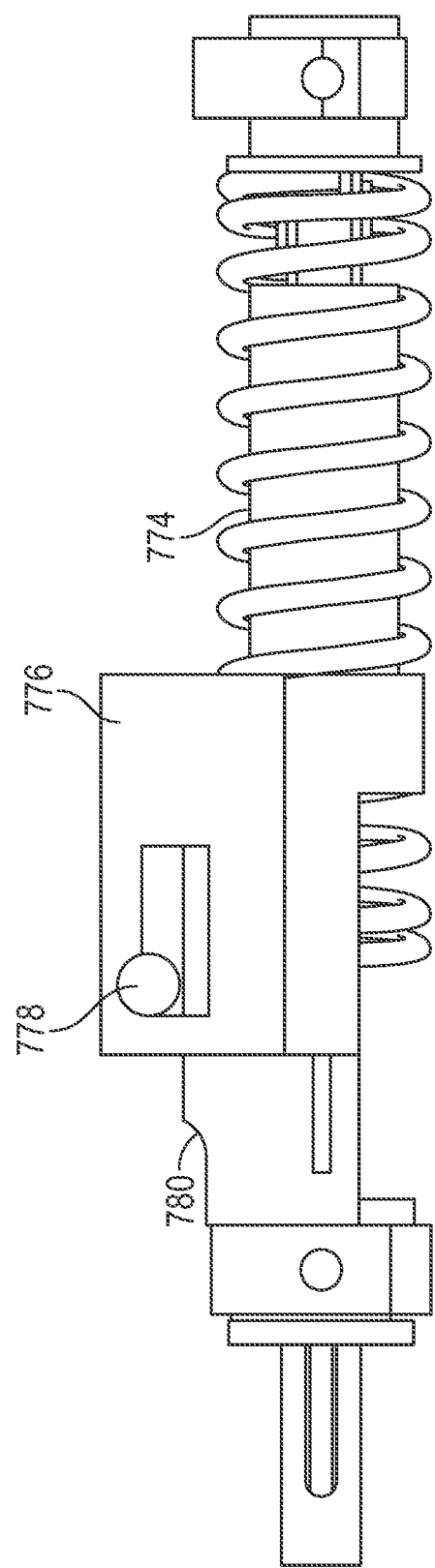
FIG. 11K is a close up view of the jaw drive mechanism showing the interlocking sleeve, according to one or more examples.
Figure 11L:
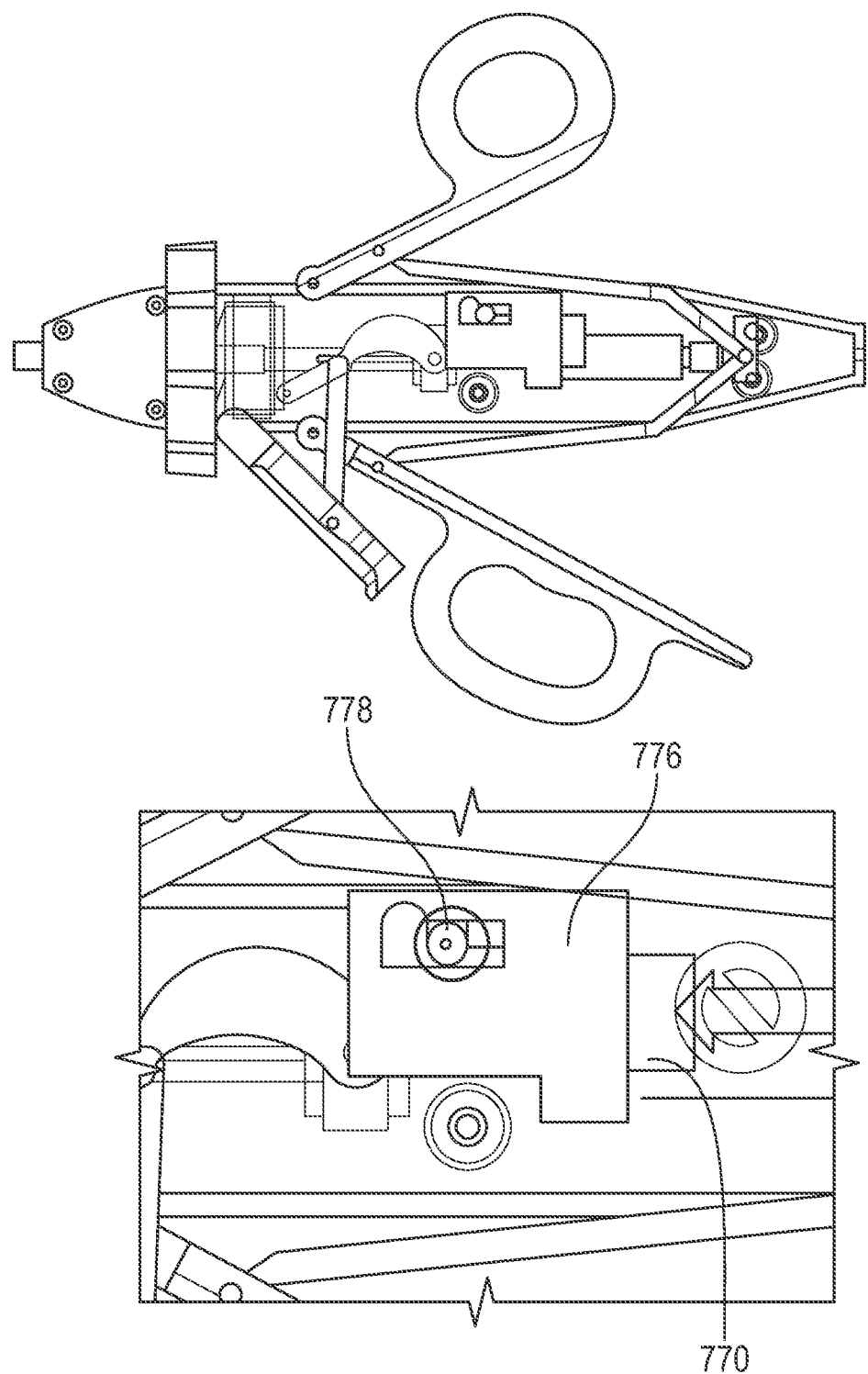
FIGS. 11L, 11M, and 11N are progressive schematic views of an interlocking system for preventing blade actuation unless the jaws are substantially closed and preventing jaws from opening unless the blade is substantially retracted, according to one more examples.
Figure 11M:
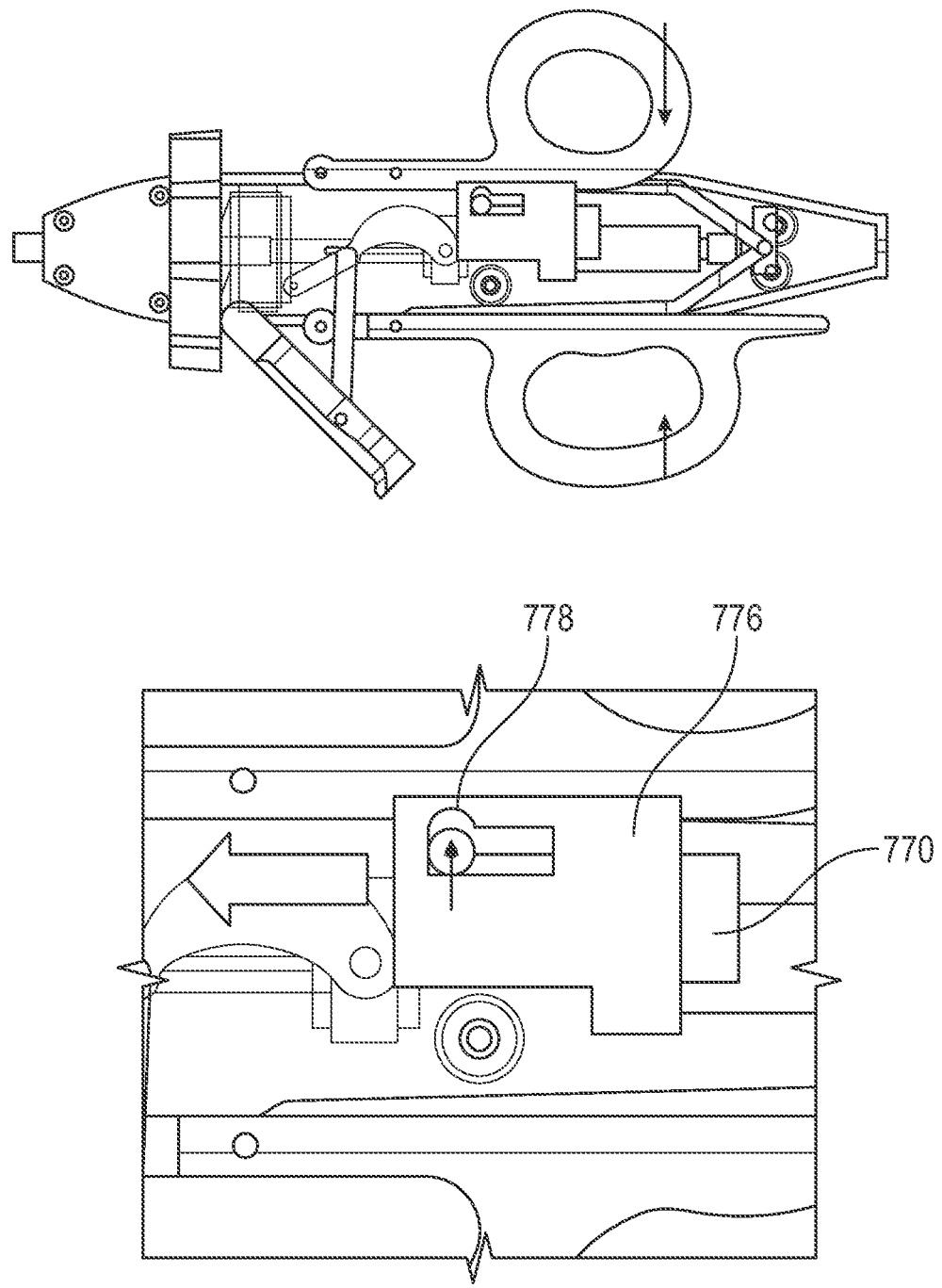
Figure 11N:
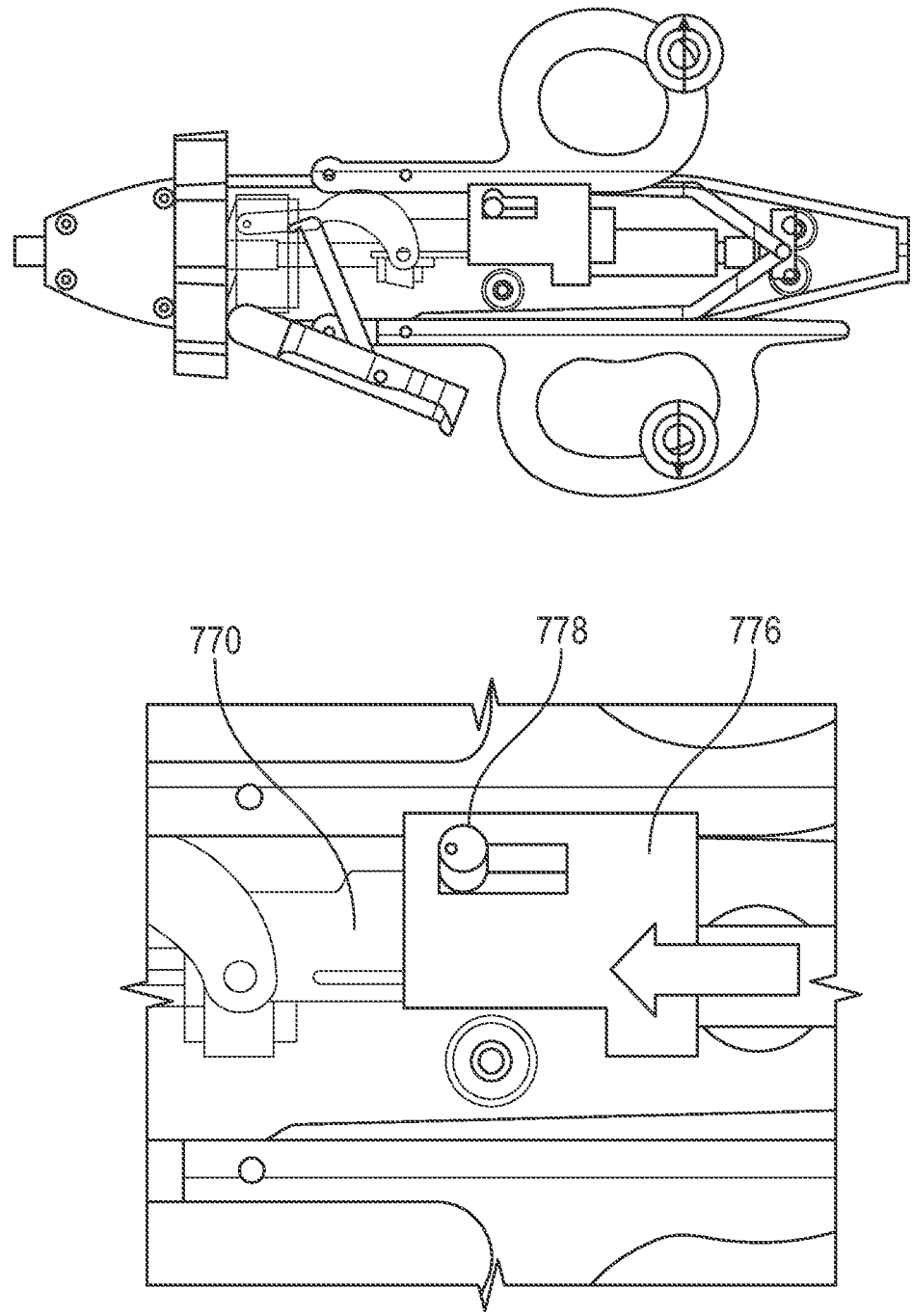
Figure 11O:
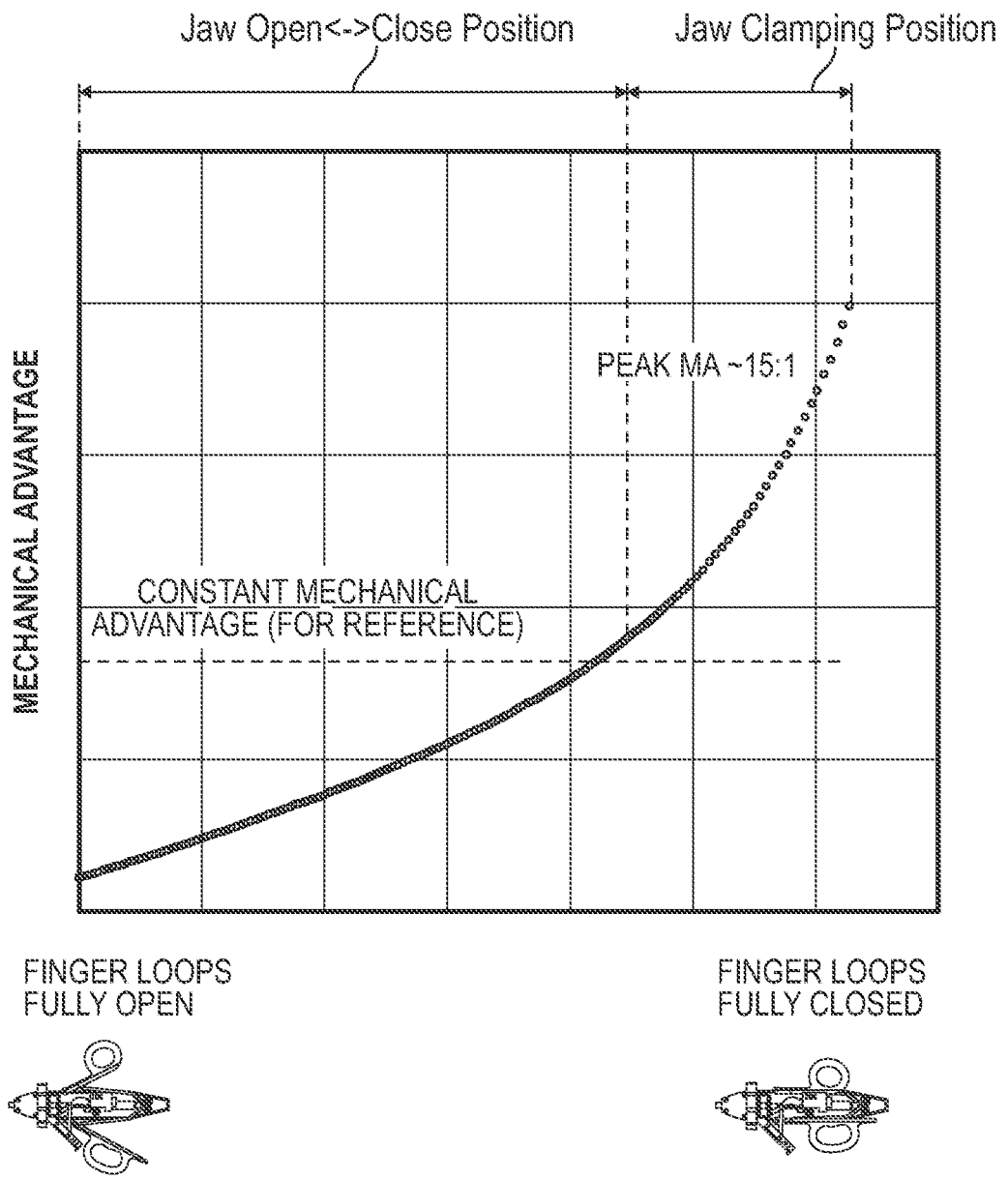
FIG. 11O is a graph depicting mechanical advantage of the jaw actuation mechanism, according to one or more examples.
Figure 11P:
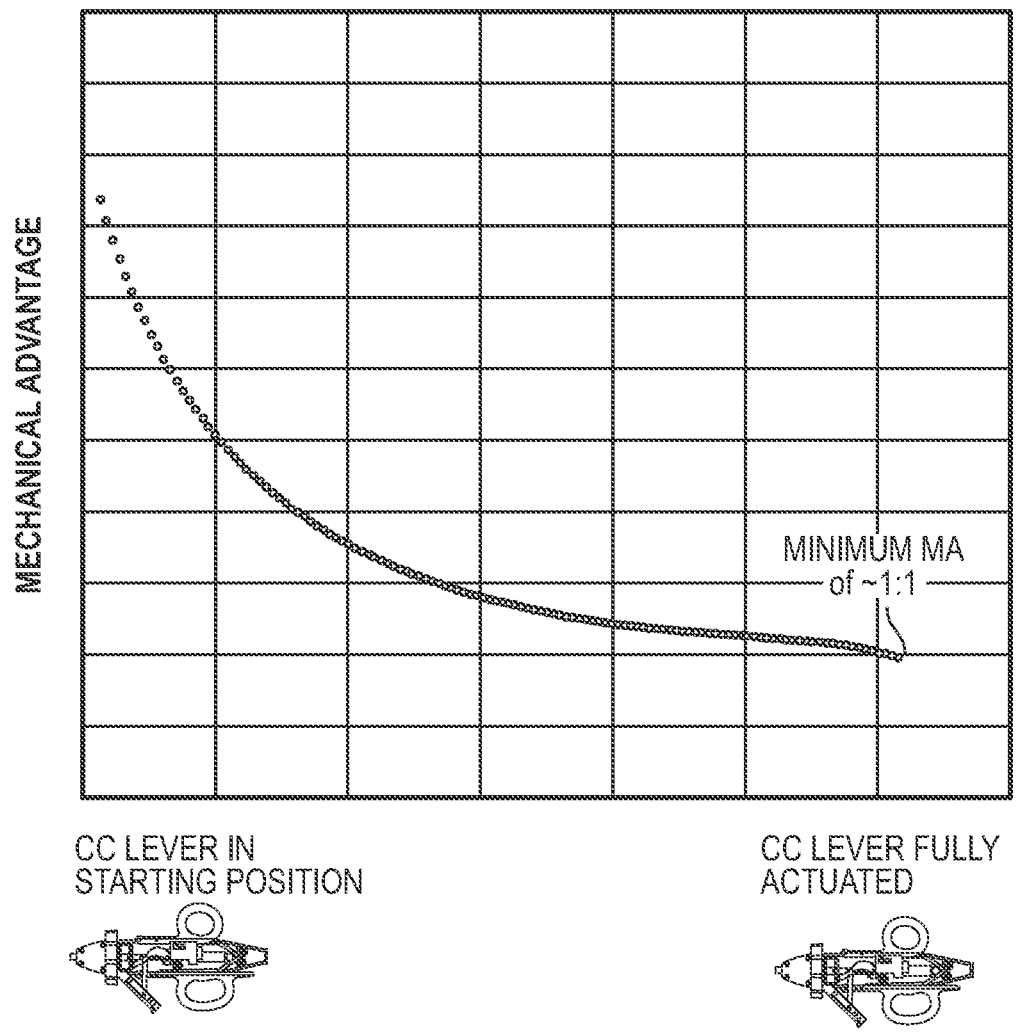
FIG. 11P is a graph depicting the mechanical advantage of the blade actuation mechanism, according to one or more examples.
Figure 11Q:
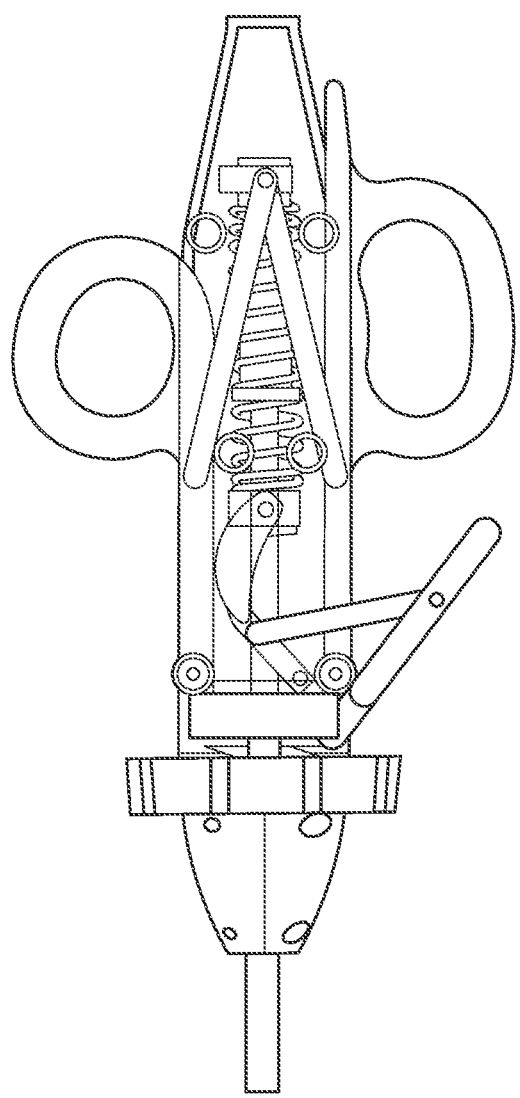
FIG. 11Q is an additional transparent view of the handle, according to one or more examples.
Figure 11R:
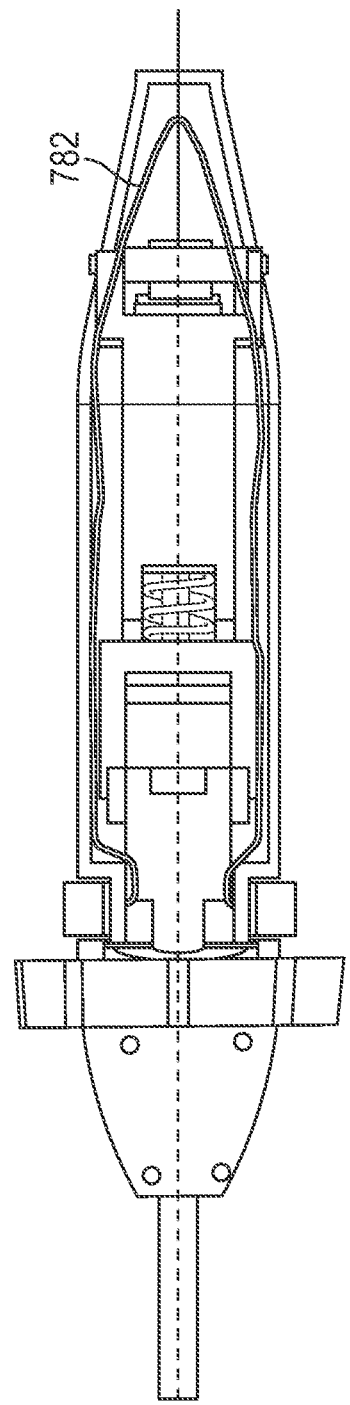
FIG. 11R is an additional transparent view of the handle, according to one or more examples.

Turning now to FIGS. 10 and 11A-11R, still another example of a medical intervention device 700 is shown. That is, FIG. 10 shows a prototype handle design and FIGS. 11A-11R show several details of an intervention device 700 incorporating a handle design that is the same or similar to the design shown in FIG. 10. It is to be appreciated that while a complete intervention device is shown in these figures (e.g., not just the handle), nothing in this document should be construed to mean that any of the previously described devices or features are mutually exclusive from the device 700. That is, one or more devices, systems, mechanisms or features of the device 100 and the several handle designs 200-600, alone or in combination, may be incorporated into the device 700.

As shown from a review of FIGS. 11A-11E, the medical intervention device 700 may include a handle 704, a medial portion 706, and a distal portion 702. As discussed above with respect to FIG. 1, distal portion 702 may include a pair of jaws 708 (see FIG. 11E) supported on a distal end 702 of the device 700 and adapted to open and close to grasp tissues, vessels, etc. The jaws 708 may have a contoured grasping surface 744 and the contoured grasping surface of each jaw 708 may complement the contoured shape of the other jaw 708 to provide full contact between the grasping surfaces when the jaws 708 are closed. In addition, and as shown, each jaw may include a slot 746 extending longitudinally along the jaw 708 to receive a cutting blade 710 that may advance out of the medial portion 706 and through the closed jaws 708. For purposes of opening and closing, the jaws 708 may also include proximally extending tabs 748 having a fixed pin 750 and arcuate slots 752. The tabs 748, including the fixed pin 750 and the arcuate slots 752 may interface with the distal end 702 of the device to cause the opening and closing of the jaws 708 as explained in more detail below.

As shown in FIGS. 11B-11D, the medial portion 706 may have an outer housing 754, an inner housing 756, and a drive rod 758. The outer housing 754 may include two distally extending arms that have a pin hole in the end and a slot arranged proximal to the pin hole. The inner housing 756 may have a slightly smaller diameter and be adapted to slide within the outer housing 754 and reciprocate longitudinally back and forth along the inside of the outer housing 754 during use. That is, actuation of the finger arms 712 between and open and closed position may advance and retract the inner housing 756 relative to the outer housing 754. The inner housing 756 may also have two distally extending arms arranged and configured to align inside the arms of the outer housing 754. The arms of the inner housing 756 may include a pin hole in an end thereof.

As may be appreciated from a review of FIG. 11E in conjunction with FIGS. 11B and 11C, the jaws 708 may be arranged in the distal end 702 of the device 700. The fixed pins on the tabs of the jaws 708 may be arranged in the pin hole at the distal end of the outer housing 754. An additional pin may be arranged in the pin holes at the distal end of the inner housing 756 and may extend through the arcuate slots 752 of the tabs 748 on the jaws 708. As the inner housing 756 reciprocates longitudinally within the outer housing 754, the pin in the distal end thereof, may slide along the arcuate slots 752 of the tabs 748 of the jaws 708 causing the jaws 708 to open and close depending on the direction of travel of the inner housing 756. That is, for example, when the inner housing 756 is drawn in a proximal direction (e.g., toward the handle 704), the jaws 708 may close and when the inner housing 756 is pushed in a distal direction (e.g., away from the handle), the jaws 708 may open. While a pin and slot configuration for the jaw operation at the distal end has been described, still other approaches to causing jaw motion may be provided.

Turning now to FIG. 11F and the trailing figures, a more detailed discussion of the handle 704 of the present example may be described. As shown, the handle 704 may include a body portion 714, a pair of finger arms 712, a cutting blade actuation interface 736, a rotation and/or articulation control knob 728/730, and an energy actuation feature 738.

The pair of finger arms may be the same or similar to those described with respect to FIG. 7 above. That is, the finger arms 712 may be the same or similar to the finger arms of FIGS. 2A and 2B without the loop tail. Nonetheless, a loop tail may be provided if desired. The energy actuation feature 738 may be the same or similar to the energy actuation feature described with respect to FIG. 6, however, the energy actuation feature 738 may be located further distal than the location shown in FIG. 6. That is, here, the energy actuation feature 738 may be arranged just proximal to the rotation or articulation control knob 728/730. The rotation and/or articulation control knob 728/730 may be arranged at the distal end of the handle 704 and may include a circumferentially extending knob 728/730 as discussed with respect to FIGS. 2A and 2B.

The cutting blade actuation interface 736 of the present example may be in the form of a single lever rather than the double lever shown in FIGS. 9A and 9B. However, and as shown, the lever may be arranged generally in plane with the finger arm 712 having the double finger loop (e.g., the finger arm adapted for engagement by the fingers of the user rather than the thumb). The lever may be arranged distally to the finger arm 712 and may have a first distal end arranged on the body 714 at a pivot point spaced distally from the pivot point of the finger arm 712. The lever may extend radially outward and proximal from the pivot point when the lever is in a non-actuated position as shown in FIG. 11F. An actuation strut 760 may extend radially inward from a pin along the lever. In one or more examples, the pin may be spaced from the pivot point of the lever and along the lever a distance of approximately 2/3 of the overall length of the lever. The strut 760 may penetrate the housing of the body 714 and engage an internal bifold mechanism 762 adapted to advance the cutting blade 710.

As shown, the bifold mechanism 762 may include a first leg 764 and a second leg 766 pivotally secured to the first leg. The strut 760 from the actuation lever may engage the bifold mechanism at or near the pivotal connection of the two legs. The first leg 764 may have an anchor end opposite the pivotal connection of the two legs where the first leg 764 is pivotally secured to the housing or body 714 and at a distal end of the bifold mechanism 762. The second leg 766 may have an actuation end opposite the pivotal connection of the two legs where the second leg 766 is pivotally secured to the drive rod or other driving mechanism of the cutting blade 710 and at a proximal end of the bifold mechanism 766. For example, as shown in FIG. 11G, the inner housing 756 may extend into the handle 704 and may include a slotted hole 768 allowing access to the drive rod 758 that may also extend into the handle 704. The inner housing 756 may have a drive interface 770 slidably arranged on the inner housing 756 with a pin or other tying element extending through the slotted hole 768 on the inner housing 756 and connected to the drive rod 758 or extending through a hole on the drive rod 758. As may be appreciated from a review of FIGS. 11L-11M, when the lever is depressed, the strut 760 may press inward on the bifold mechanism 762 causing the bifold mechanism to fold where the first leg 764 and second leg 766 pivot with respect to one another about the pivotal connection of the two legs. Since the distal end of the bifold mechanism 762 is secured to the housing, the folding action of the bifold mechanism 762 may draw the proximal end of the bifold mechanism 762 in a distal direction. This motion may pull the drive interface 770 in a distal direction relative to the inner housing 756 and the pin or other tying element arranged in the slot 768 of the inner housing 756 may cause the drive rod 758 to move in a distal direction thereby advancing the cutting blade 710 at the distal end 702 of the device 700. As shown in FIGS. 11F and 11N, the second leg 766 of the bifold mechanism 762 may include an outer curved cam surface that may be adapted to provide clearance and avoid the central rod and inner housing when actuating the mechanism. An interlock system may also be provided that prevents actuation of the lever unless/until the finger arms are substantially closed. This is discussed in more detail below after the finger arm mechanism is described.

The mechanism for opening and closing the jaws 708 may be described with respect to FIGS. 11F and 11I. For example, as shown, the finger arms 712 may be pivotally secured to the housing or body 714 at a distal end of the finger arms 712 and the arms 712 may, thus, be adapted to open and close by pivoting about their respective pivotal attachments. A tie rod 772 may extend in a proximal direction from a point relatively distally arranged on each of the finger arms 712. The tie rods 772 may extend to a proximal end of the inner housing 756 and be pivotally secured to the proximal end of the inner housing 756 at a jaw drive interface 774, for example. In one or more embodiments, as shown in FIG. 11F, the tie rods 772 may include a kink or bend in them allowing them to avoid interacting with other components within the handle 704 when the finger arms 712 are in a closed position. As may be appreciated from a review of FIGS. 11F and 11I, when the finger arms 712 are opened, the tie rods 772 may be drawn forward. Their connection to the proximal end of the inner housing 756 may urge the inner housing 756 in a distal direction. As discussed above, with respect to FIGS. 11B and 11C, when the inner housing 756 is driven distally, the jaws 708 may open. When the finger arms 712 are squeezed together, the proximal end of the tie rods 772 may be driven in a proximal direction thereby pulling the inner housing 756 in a proximal direction and closing the jaws 708.

Referring now to FIGS. 11K-11N, an interlock system that may prevent or resist actuation of the cutting blade in particular circumstances may be provided. As shown, the interlock may include a sleeve 776 arranged over the cutting blade drive interface 770. As shown in FIG. 11K, the sleeve 776 may be a part of the jaw drive interface 774 or be otherwise secured to the inner housing 756 which is actuatable by the finger arms 712. The sleeve 776 may include an internal raceway for containing a bearing, roller, or pin 778 as shown in FIGS. 11L-11N. The raceway may include a relief notch at a distal end. Moreover, the drive interface 770 may include an outer surface with a distal ramp 780. When the finger arms 712 are open and, as such, the inner housing 756 and sleeve 776 is arranged in a distal position, the bearing or roller 778 may be held relatively tightly against the drive interface 770 in a position distal to the distal ramp 780. That is, the bearing or roller 778 may be arranged in the raceway in a position that is not aligned with the relief notch as shown in FIG. 11L. However, as the fingers 712 are closed, the inner housing 756 and sleeve 776 may move in a proximal direction, bringing the relief notch of the sleeve 776 into alignment with the bearing or roller 778 and allowing the bearing or roller 778 to move radially outward under force or pressure from a distally advancing ramp 780 on the drive interface 770 as shown in FIG. 11M. With freedom of the bearing or roller 778 to move radially outward, the drive interface 770 may force the bearing or roller 778 radially outward, which may clear the ramp 780 of the drive interface 770 and allow the drive interface 770, the drive rod 758, and the blade 710 to advance under the force of the actuation lever. It is to be appreciated that this outward motion of the bearing or roller 778 may also lock the sleeve 776 and, thus, the inner housing 756 against motion as shown in FIG. 11N. That is, when the bearing roller 778 moves radially outward, it may create an engagement between the sleeve 776 and housing or body 714 that prevents the sleeve 776 from moving, which, in turn prevents the inner housing 756 and the finger arms 712 from moving.

FIG. 11O is a diagram of the mechanical advantage provided by the finger arm mechanism. That is, connection of the tie rod 772 to the finger arm 712 at a point relatively distal on the finger arm 712 and closer to the pivot point of the finger arm 712 than the finger ring, provides a mechanical advantage that magnifies the user's pressing force to a much higher force experienced by the tie rod 772. Moreover, as the tie rod angle relative to the finger arm angle decreases, the force applied to the finger ring generates a much higher compression in the tie rod due to the component of force within the tie rod being at such a shallow angle relative to the finger arm. As shown in FIG. 11O, as the jaws 708 approach a clamping position, the mechanical advantage of the finger arms 712 may be approximately 15:1, for example. That is, for every unit of force applied at the finger arms 712, the jaws 708 may experience 15 units of force.

FIG. 11P is a diagram of the mechanical advantage provided by the cutting lever. Here, the mechanical advantage may decrease as the cutting stroke is completed, which may provide for a strong cutting action at the beginning of a cut and a weaker cutting action at the end of a cut. Here the lever is engaged by a strut 760 that is secured to the lever closer to the pressing end than the pivot end. Nonetheless, the strut force may exceed the users's depressing force providing some initial level of mechanical advantage (albeit not as much as the finger arm advantage). As the strut 760 carries the compressive depressing force to the bifold mechanism 762, the bifold mechanism 762 may be in a relatively flat orientation. The compressive force in the strut 760 is counteracted by tension in the legs 766 of the bifold mechanism 762, but the tension is acting at a very flat angle relative to the strut force, which is directed laterally. As such, a relatively small amount of compression in the strut 760 induces a high amount of tension in the legs 766 of the bifold mechanism, which generates a high cutting force. However, as the cutting motion continues, the legs 766 of the bifold mechanism 762 begin to align with or at least approach a more aligned condition with the strut 760, so compression in the strut 760 begins to induce less tension in the legs 766 and less of a cutting blade driving force. As shown, the ending driving force may have a mechanical advantage close to 1:1, for example.

FIGS. 11Q and 11R shown additional details of the handle. In particular, FIG. 11R shows energizing wire 782 routing that may function to supply power to the handle allowing the energy actuation interface to supply power to electrodes on the jaws when the button is depressed. That is, for example the clamping surfaces of the jaws may include electrodes and supplying the electrodes with electrical energy may allow for cauterizing or other heat-based treatments to be provided or performed.

Figure 12B:
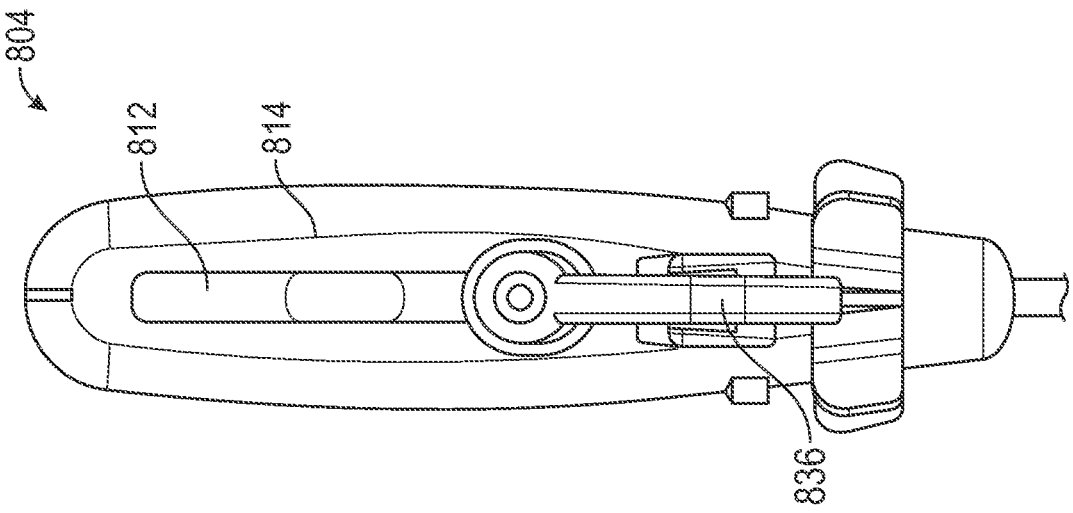
FIG. 12B is an additional side view of the handle portion of FIG. 12A, according to one or more examples.
Figure 12A:
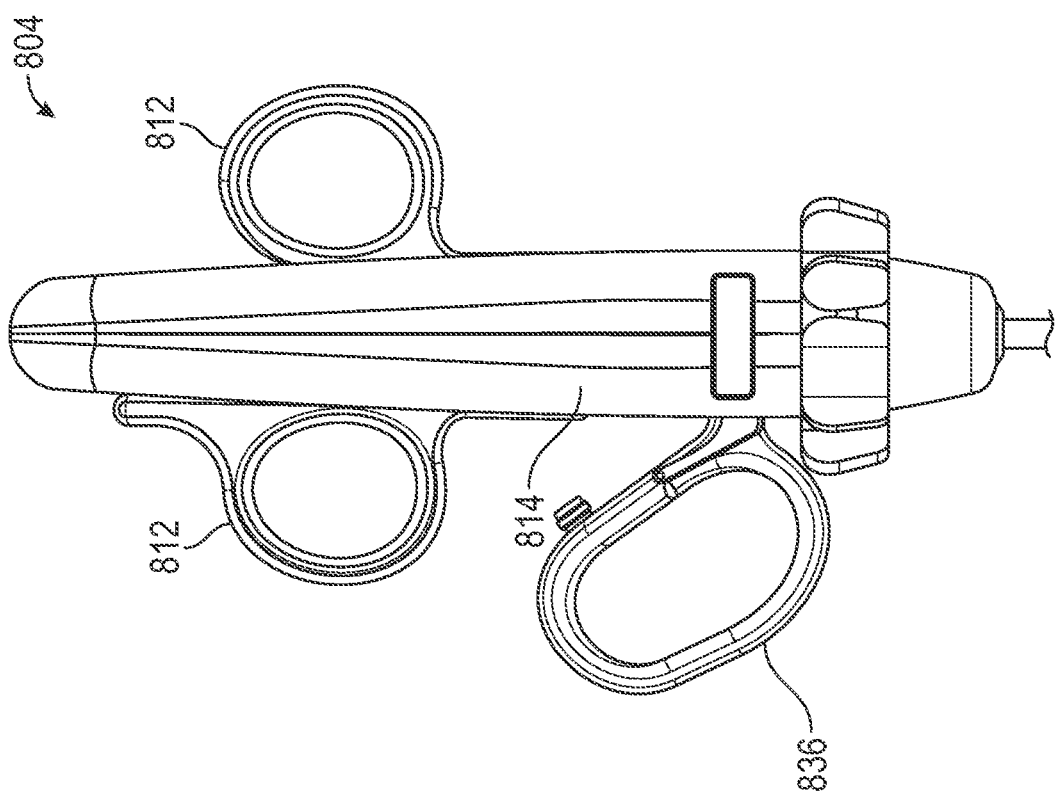
FIG. 12A is a side view of a handle portion of a medical intervention device, according to one or more examples.
Figure 12D:
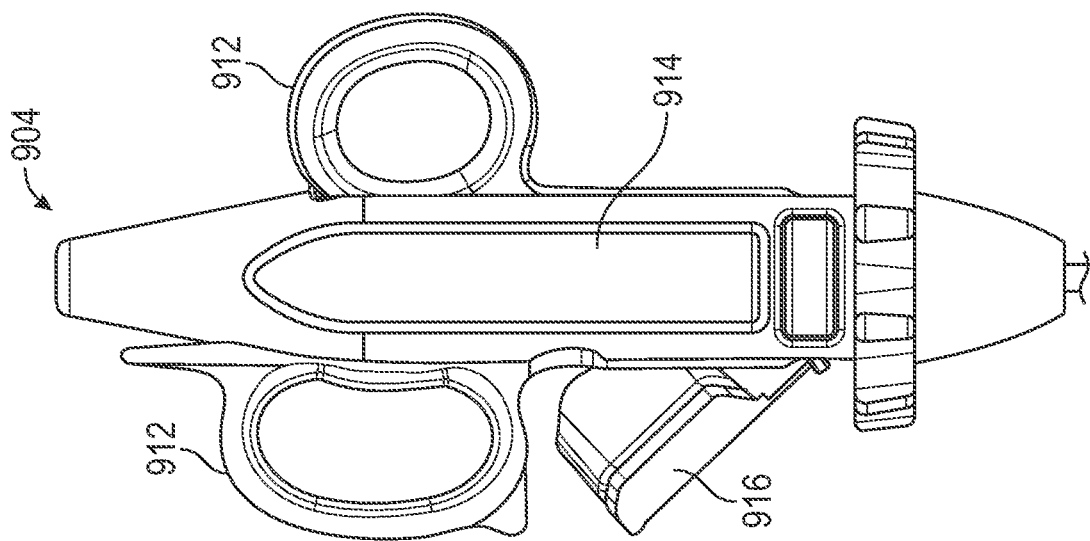
FIG. 12D is a side view of a handle portion of a medical intervention device, according to one or more examples.
Figure 12C:
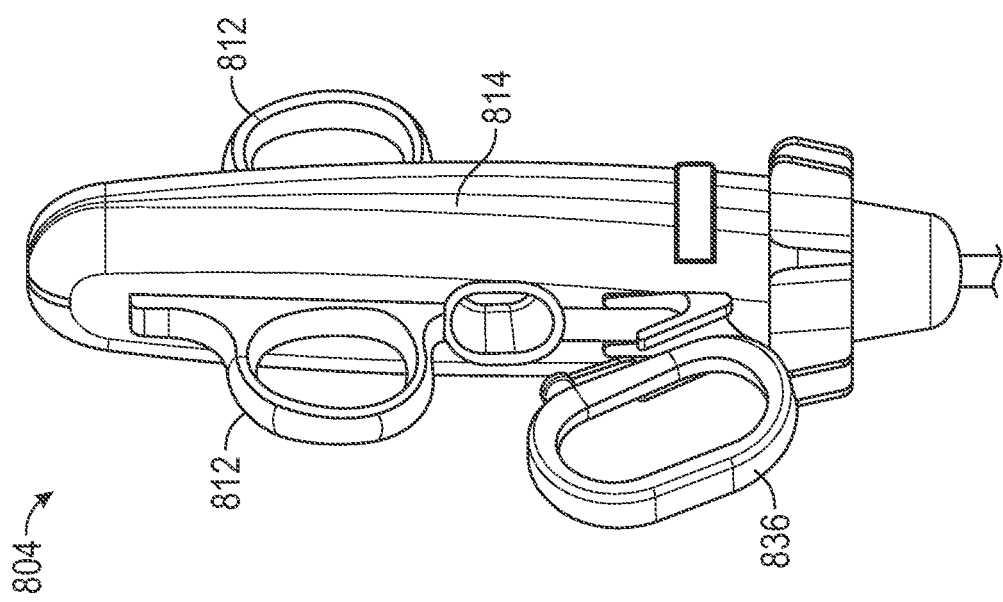
FIG. 12C is a perspective view thereof.

FIGS. 12A-12C show yet another example of a handle 804 for a medical intervention device such as that of FIG. 1. This embodiment may share features of the example of FIGS. 2A and 2B as well as the example of FIGS. 6, 7, 8A, 8B, 9A, 9B, 10, and 11A-11R and may also have the same or similar inner working elements such as those described with respect to FIGS. 3-5. Moreover, while particular elements are shown and described, similar elements of the earlier described examples may be substituted for the elements shown.

In the present example, finger arms 812 may be provided that are the same or similar to those described with respect to FIG. 11A. However, the finger loop 818 may be slightly smaller (e.g., a single finger loop) than the finger loop of FIG. 11A providing more space along the handle for the cutting blade actuation interface 836. That is, the cutting blade actuation interface 836 of the present example may be in the form of a lever similar to that of the interface 736 and may be arranged generally in plane with the finger arm 812 having the finger loop with the extension portion (e.g., the finger arm adapted for engagement by the fingers of the user rather than the thumb). The lever may be arranged distally to the finger arm 812 and may have a first distal end arranged on the body 814 at a pivot point spaced distally from the pivot point of the finger arm 812. The lever may extend radially outward and proximal from the pivot point when the lever is in a non-actuated position as shown in FIG. 12A. The interface 836 may include a loop on the lever that may be sized for multiple fingers such as, for example, the pinky and ring finger, for example. In addition, the lever may include a body facing plug or pin that may be adapted for receipt by a detent or other recess on the body, when the interface 836 is actuated and/or pulled/pivoted inward toward the body 814. Other internal mechanisms and actuation features may be the same or similar to the handle of FIGS. 11A-11R.

FIGS. 12D-12F show yet another example of a handle 904 for a medical intervention device such as that of FIG. 1. This embodiment may share features of the example of FIGS. 2A and 2B as well as the example of FIGS. 6, 7, 8A, 8B, 9A, 9B, 10, 11A-11R, and 12A-12C and may also have the same or similar inner working elements such as those described with respect to FIGS. 3-5. Moreover, while particular elements are shown and described, similar elements of the earlier described examples may be substituted for the elements shown.

In the present example, finger arms 912 may be provided that are the same or similar to those shown with respect to FIGS. 10 and 11A-11R. Moreover, a single lever type of cutting blade actuation interface 936 may also be provided like FIGS. 11A-11R and FIGS. 12A-12C. However, the interface 936 may include flanking sides that extend from a pressing surface of the lever and return toward the body portion 914 of the handle 904. The flanking sides may assist with alignment of the lever as the lever articulates about its pivot point. That is, the flanking sides may be sized and positioned to pass along the outside surface of the handle and maintain the alignment of the interface 936. Other internal mechanism and actuation features may be the same or similar to the handle of FIGS. 11A-11R.

The directional descriptors described herein are used with their normal and customary use in the art. For example, proximal, distal, lateral, up, down, top and bottom may be used to describe the apparatus with the longitudinal axis arranged parallel to a ground with the device in an upright position. The proximal direction refers to a direction towards the user end of the apparatus, and the distal direction represents a direction towards the patient end of the apparatus.

Relative terms described herein, such as, "about" or "substantially" may be used to indicate a possible variation of ±10% in a stated numeric value, or a manufacturing variation.

As described throughout this disclosure, components and assemblies can be operably connected to each other and interact with one another in a manner that provides improved actuation, a more compact and simpler design, lower cost, and better user satisfaction than traditional medical devices.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A medical intervention device, comprising:
   a distal end comprising a pair of jaws;
   a handle operably coupled to the distal end and comprising:
   a pair of pivoting finger arms each connected to the handle at a pivot point and extending proximally to at least one finger loop, the pivoting finger arms being configured for opening and closing the pair of jaws at the distal end; and
   at least one actuation interface arranged on the handle and in a position distal to the respective pivot points of the pair of pivoting finger arms.

2. The medical intervention device of claim 1, wherein the device is configured for use in a generally horizontal orientation and a generally vertical orientation depending on a type of procedure being performed.

3. The medical intervention device of claim 1, wherein the at least one actuation interface is a cutting blade actuation interface.

4. The medical intervention device of claim 3, wherein the cutting blade actuation interface comprises a lever.

5. The medical intervention device of claim 4, further comprising an interlock that prevents actuation of the lever unless the jaws are substantially closed.

6. The medical intervention device of claim 4, wherein the lever comprises a pair of levers.

7. The medical intervention device of claim 3, wherein the cutting blade actuation interface comprises two cutting blade actuation interfaces.

8. The medical intervention device of claim 1, wherein the at least one actuation interface is an energy actuation feature.

9. The medical intervention device of claim 1, wherein the at least one actuation interface is a rotation control knob.

10. The medical intervention device of claim 1, wherein the at least one actuation interface is an articulation control knob.

11. The medical intervention device of claim 1, wherein motion of a first finger arm of the pair of finger arms is dependent on motion a second finger arm of the pair of finger arms.

12. The medical intervention device of claim 11, further comprising a motion converting slide for establishing the dependent motion of the pair of finger arms.

13. The medical intervention device of claim 1, wherein the device comprises a cutting blade at a distal end and actuation of the cutting blade is performed by moving the pivoting finger arms through a selected range of motion.

14. A handle for controlling a distal end of a medical intervention device, the handle comprising:
a body;
a pair of pivoting finger arms each pivotally secured to the body at a pivot point and each having at least one finger loop, the pivoting finger arms being configured for opening and closing a pair of jaws at the distal end; and
at least one actuation interface arranged on the handle and in a position distal to the respective pivot points of the pair of pivoting finger arms.

15. A medical intervention device, comprising:
a distal end comprising a pair of jaws;
a handle operably coupled to the distal end and comprising:
a pair of pivoting finger arms configured for opening and closing the pair of jaws at the distal end and having an arm linkage system arrange between them defining at least one pivot point at a distal end of the pair of pivoting finger arms and;
a rotation control knob distal of the pivot point and configured for controlling rotation of the pair of jaws; and
an articulation control knob distal of the pivot point and configured for controlling articulation of the pair of jaws.

16. The medical intervention device of claim 15, wherein the linkage system is such that motion of a first finger arm of the pair of finger arms is dependent on motion a second finger arm of the pair of finger arms.

17. The medical intervention device of claim 16, further comprising a motion converting slide for establishing the dependent motion of the pair of finger arms.

18. The medical intervention device of claim 15, wherein the pair of pivoting finger arms each comprise at least one finger loop.

* * * * *